US011261140B2

United States Patent
Sangar et al.

(10) Patent No.: US 11,261,140 B2
(45) Date of Patent: Mar. 1, 2022

(54) PROCESSES AND SYSTEMS FOR THE CONVERSION OF ACYCLIC HYDROCARBONS TO CYCLOPENTADIENE

(71) Applicant: ExxonMobil Chemical Patents Inc., Baytown, TX (US)

(72) Inventors: Neeraj Sangar, League City, TX (US); Larry L. Iaccino, Seabrook, TX (US); Christopher L. Becker, Manhattan, KS (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 36 days.

(21) Appl. No.: 16/639,918

(22) PCT Filed: Jun. 5, 2018

(86) PCT No.: PCT/US2018/036117
§ 371 (c)(1),
(2) Date: Feb. 18, 2020

(87) PCT Pub. No.: WO2019/055076
PCT Pub. Date: Mar. 21, 2019

(65) Prior Publication Data
US 2020/0239384 A1    Jul. 30, 2020

Related U.S. Application Data

(60) Provisional application No. 62/558,437, filed on Sep. 14, 2017.

(51) Int. Cl.
*C07C 2/84*    (2006.01)
*B01J 19/00*   (2006.01)
(Continued)

(52) U.S. Cl.
CPC ............. *C07C 2/84* (2013.01); *B01J 19/0013* (2013.01); *B01J 19/2445* (2013.01);
(Continued)

(58) Field of Classification Search
CPC .......... C07C 2/84; C07C 5/52; B01J 19/0013; B01J 19/2445; B01J 19/2485;
(Continued)

(56) References Cited

U.S. PATENT DOCUMENTS 2,438,398 A    3/1948   Kennedy et al.
2,438,399 A    3/1948   Kennedy et al.
(Continued)

FOREIGN PATENT DOCUMENTS

EP    1213052 A1 *  6/2002   ............ B01J 8/0465
WO    2017/078894 A1   5/2017

OTHER PUBLICATIONS

Fel'dblyum, V.S., et al. "Cyclization and Dehydrocyclization of C5 Hydrocarbons over Platinum Nanocatalysts and in the Presence of Hydrogen Sulfide," Doklady Chemistry, 2009, vol. 424, pp. 27-30.
(Continued)

*Primary Examiner* — Ali Z Fadhel

(57) ABSTRACT

This invention relates to processes and systems for converting acyclic hydrocarbons to alkenes, cyclic hydrocarbons and/or aromatics, for example converting acyclic $C_5$ hydrocarbons to cyclopentadiene in a reactor system. The process includes heating an electrically-conductive reaction zone by applying an electrical current to the first electrically-conductive reaction zone; and contacting a feedstock comprising acyclic hydrocarbons with a catalyst material in the electrically-conductive reaction zone under reaction conditions to convert at least a portion of the acyclic hydrocarbons to an effluent comprising alkenes, cyclic hydrocarbons, and/or aromatics.

24 Claims, 2 Drawing Sheets

(51) Int. Cl.
    *B01J 19/24*      (2006.01)
    *C07C 5/52*       (2006.01)
(52) U.S. Cl.
    CPC ............ *B01J 19/2485* (2013.01); *C07C 5/52*
        (2013.01); *B01J 2219/00038* (2013.01); *B01J*
                    *2219/00135* (2013.01); *B01J 2219/185*
            (2013.01); *B01J 2219/1923* (2013.01)
(58) Field of Classification Search
    CPC .... B01J 2219/00038; B01J 2219/00135; B01J
                2219/185; B01J 2219/1923; B01J 23/42;
                B01J 29/26; B01J 29/46; B01J 29/90;
                B01J 2208/00389; B01J 2208/00398;
                B01J 2208/00415; B01J 2219/0809; B01J
                    2219/0871; B01J 2219/0875; B01J
                    2219/0892; B01J 8/0242; B01J 8/048;
                B01J 8/0496; B01J 38/10; B01J 38/12;
                B01J 19/08; B01J 8/0285; B01J 29/44;
                                                Y02P 20/584
    See application file for complete search history.

(56) References Cited

U.S. PATENT DOCUMENTS

| | | | |
|---|---|---|---|
| 2,438,400 A | 3/1948 | Kennedy et al. | |
| 2,438,401 A * | 3/1948 | Kennedy et al. | ....... C07C 5/373 |
| | | | 585/366 |
| 2,438,402 A | 3/1948 | Kennedy et al. | |
| 2,438,403 A | 3/1948 | Kennedy et al. | |
| 2,438,404 A | 3/1948 | Hetzel et al. | |
| 2,982,798 A | 5/1961 | Hachmuth et al. | |
| 3,953,368 A | 4/1976 | Sinfelt | |
| 4,108,911 A | 8/1978 | Wideman et al. | |
| 5,192,728 A | 3/1993 | Dessau | |
| 5,254,787 A | 10/1993 | Dessau | |
| 5,284,986 A | 2/1994 | Dessau | |
| 5,633,421 A | 5/1997 | Iezzi et al. | |
| 6,623,707 B1 * | 9/2003 | Addiego | ................ B01J 8/0419 |
| | | | 422/198 |
| 2010/0305374 A1 | 12/2010 | Iaccino et al. | |
| 2012/0065443 A1 * | 3/2012 | Mabande | ................ B01J 23/96 |
| | | | 585/430 |
| 2015/0152024 A1 | 6/2015 | Iitsuka et al. | |
| 2018/0311630 A1 * | 11/2018 | Hojlund Nielsen | ... B01J 8/0285 |
| 2020/0290003 A1 * | 9/2020 | Hojlund Nielsen | ..... B01J 29/85 |

OTHER PUBLICATIONS

Bricker, J.C. et al., "Advanced Catalytic Dehydrogenation Technologies for Production of Olefins," Topics in Catalysis, 2012, vol. 55, pp. 1309-1314.
Vora, B.V., "Development of Dehydrogenation Catalysts and Processes," Topics in Catalysis, 2012, vol. 55, pp. 1297-1308.
Kanazirev, V., et al. "Conversion of C8 Aromatics and n-Pentane Over Ga2O3/HZSM-5 Mechanically Mixed Catalysts," Catalysis Letters, 1991, vol. 9, pp. 35-42.
Xu, Y., "Methane activation without using oxidants over Mo/HZSM-5 zeolite catalysts," Catalysis Letters, 1994, vol. 30, pp. 135-149.
Kennedy, R.M. et al., "Formation of Cyclopentadiene from 1,3-Pentadiene," Industrial and Engineering Chemistry, 1950, vol. 42, No. 3, pp. 547-552.
Lopez, C.M., et al. "n-Pentane Hydroisomerization on Pt Containing HZSM-5, HBEA and SAPO-11," Catalysis Letters, 2008, vol. 122, pp. 267-273.
Marcinkowski, T.E., "Isomerization and Dehydrocyclization of 1,3-Pentadiene," M.S., University of Central Florida, 1979.
Li et al. in "Catalytic Dehydroisomerization of n-alkanes to Isoalkenes," Journal of Catalysis, 2008, vol. 255, pp. 134-137.

* cited by examiner

PROCESSES AND SYSTEMS FOR THE CONVERSION OF ACYCLIC HYDROCARBONS TO CYCLOPENTADIENE

CROSS-REFERENCE OF RELATED APPLICATIONS

This application is a National Phase Application claiming priority to PCT Application Serial No. PCT/US2018/036117, filed Jun. 5, 2018, which claims priority to U.S. Provisional Application Ser. No. 62/558,437, filed Sep. 14, 2017, the disclosures of which are incorporated herein by reference.

FIELD OF THE INVENTION

This invention relates to processes and reactor systems for the conversion of acyclic hydrocarbons to alkenes, cyclic hydrocarbons, and/or aromatics.

BACKGROUND OF THE INVENTION

Cyclic hydrocarbons, alkenes, and aromatics, such as cyclopentadiene ("CPD") and its dimer dicyclopentadiene ("DCPD"), ethylene, propylene, and benzene, are highly desired raw materials used throughout the chemical industry in a wide range of products, for example, polymeric materials, polyester resins, synthetic rubbers, solvents, fuels, fuel additives, etc. These compounds are typically derived from various streams produced during refinery processing of petroleum. In particular, CPD is currently a minor byproduct of liquid fed steam cracking (e.g., naphtha, and heavier feed). As existing and new steam cracking facilities shift to lighter feeds, less CPD is produced while demand for CPD is rising. High cost due to supply limitations impacts the potential end product use of CPD in polymers. More CPD-based polymer product could be produced if additional CPD could be produced at unconstrained rates and preferably at a cost lower than recovery from steam cracking. When producing CPD, co-production of other cyclic $C_5$ compounds is also desirable. In particular, cyclopentane and cyclopentene can have high value as solvents while cyclopentene may be used as a comonomer to produce polymers and as a starting material for other high value chemicals.

It would be advantageous to be able to produce these cyclic hydrocarbons, alkenes, and aromatics, including CPD, propylene, ethylene, and benzene, as the primary product from plentiful hydrocarbon feedstock. When producing CPD, it is also desirable to minimize production of light ($C_{4-}$) byproducts. While a feedstock composed of lower hydrogen content (e.g., cyclics, alkenes, and dialkenes) could be preferred because the reaction endotherm is reduced and thermodynamic constraints on conversion are improved, non-saturates are more expensive than saturate feedstock. Further, an abundance of saturate hydrocarbons, such as $C_5$ hydrocarbons, are available from unconventional gas and shale oil, as well as reduced use in motor fuels due to stringent environmental regulations. Various hydrocarbon feedstocks, such as $C_5$ feedstock, may also be derived from bio-feeds. Linear hydrocarbon skeletal structure is preferred over branched hydrocarbon skeletal structures due to both reaction chemistry and the lower value of linear hydrocarbon relative to branched hydrocarbon (due to octane differences).

Various catalytic dehydrogenation technologies are currently used to produce mono- and di-olefins from $C_3$ and $C_4$ alkanes, but not cyclic mono-olefins or cyclic di-olefins. A typical process uses Pt/Sn supported on alumina as the active catalyst. Another useful process uses chromia on alumina. See, B. V. Vora, "Development of Dehydrogenation Catalysts and Processes," Topics in Catalysis, vol. 55, pp. 1297-1308, 2012; and J. C. Bricker, "Advanced Catalytic Dehydrogenation Technologies for Production of Olefins," Topics in Catalysis, vol. 55, pp. 1309-1314, 2012.

Still another common process uses Pt/Sn supported on Zn and/or Ca aluminate to dehydrogenate propane. While these processes are successful in dehydrogenating alkanes, they do not perform cyclization, which is critical to producing CPD. Pt—Sn/alumina and Pt—Sn/aluminate catalysts exhibit moderate conversion of n-pentane, but such catalyst have poor selectivity and yield to cyclic $C_5$ products.

Pt supported on chlorided alumina catalysts are used to reform low octane naphtha to aromatics such as benzene and toluene. See, U.S. Pat. No. 3,953,368 (Sinfelt), "Polymetallic Cluster Compositions Useful as Hydrocarbon Conversion Catalysts." While these catalysts are effective in dehydrogenating and cyclizing $C_6$ and higher alkanes to form $C_6$ aromatic rings, they are less effective in converting acyclic $C_5$s to cyclic $C_5$s. These Pt supported on chlorided alumina catalysts exhibit low yields of cyclic $C_5$ and exhibit deactivation within the first two hours of time on stream. Cyclization of $C_6$ and $C_7$ alkanes is aided by the formation of an aromatic ring, which does not occur in $C_5$ cyclization. This effect may be due in part to the much higher heat of formation for CPD, a cyclic $C_5$, as compared to benzene, a cyclic $C_6$, and toluene, a cyclic $C_7$. This is also exhibited by Pt/Ir and Pt/Sn supported on chlorided alumina. Although these alumina catalysts perform both dehydrogenation and cyclization of $C_{6+}$ species to form $C_6$ aromatic rings, a different catalyst will be needed to convert acyclic $C_5$ to cyclic $C_5$.

Ga-containing ZSM-5 catalysts are used in a process to produce aromatics from light paraffins. A study by Kanazirev et al. showed n-pentane is readily converted over $Ga_2O_3$/H-ZSM-5. Kanazirev Price et al., "Conversion of $C_8$ aromatics and n-pentane over $Ga_2O_3$/H-ZSM-5 mechanically mixed catalysts," Catalysis Letters, vol. 9, pp. 35-42, 1991. No production of cyclic $C_5$ was reported while upwards of 6 wt % aromatics were produced at 440° C. and 1.8 $hr^{-1}$ WHSV. Mo/ZSM-5 catalysts have also been shown to dehydrogenate and/or cyclize paraffins, especially methane. See, Y. Xu, S. Liu, X. Guo, L. Wang, and M. Xie, "Methane activation without using oxidants over Mo/HZSM-5 zeolite catalysts," Catalysis Letters, vol. 30, pp. 135-149, 1994. High conversion of n-pentane using Mo/ZSM-5 was demonstrated with no production of cyclic $C_5$ and high yield to cracking products. This shows that ZSM-5-based catalysts can convert paraffins to a $C_6$ ring, but not necessarily to produce a $C_5$ ring.

U.S. Pat. No. 5,254,787 (Dessau) introduced the NU-87 catalyst used in the dehydrogenation of paraffins. This catalyst was shown to dehydrogenate $C_2$-$C_{6+}$ to produce their unsaturated analogs. A distinction between $C_{2-5}$ and $C_{6+}$ alkanes was made explicit in this patent: dehydrogenation of $C_{2-5}$ alkanes produced linear or branched mono-olefins or di-olefins, whereas dehydrogenation of $C_{6+}$ alkanes yielded aromatics. U.S. Pat. No. 5,192,728 (Dessau) involves similar chemistry, but with a tin-containing crystalline microporous material. As with the NU-87 catalyst, $C_5$ dehydrogenation was only shown to produce linear or branched, mono-olefins or di-olefins and not CPD.

U.S. Pat. No. 5,284,986 (Dessau) introduced a dual-stage process for the production of cyclopentane and cyclopentene from n-pentane. An example was conducted wherein the first stage involved dehydrogenation and dehydrocyclization of n-pentane to a mix of paraffins, mono-olefins and di-olefins, and naphthenes over a Pt/Sn-ZSM-5 catalyst. This mixture was then introduced to a second-stage reactor consisting of Pd/Sn-ZSM-5 catalyst where dienes, especially CPD, were converted to olefins and saturates. Cyclopentene was the desired product in this process, whereas CPD was an unwanted byproduct.

U.S. Pat. Nos. 2,438,398; 2,438,399; 2,438,400; 2,438,401; 2,438,402; 2,438,403; and 2,438,404 (Kennedy) disclosed production of CPD from 1,3-pentadiene over various catalysts. Low operating pressures, low per pass conversion, and low selectivity make this process undesirable. Additionally, 1,3-pentadiene is not a readily available feedstock, unlike n-pentane. See also, Kennedy et al., "Formation of Cyclopentadiene from 1,3-Pentadiene," Industrial & Engineering Chemistry, vol. 42, pp. 547-552, 1950.

Fel'dblyum et al. in "Cyclization and dehydrocyclization of $C_5$ hydrocarbons over platinum nanocatalysts and in the presence of hydrogen sulfide," *Doklady Chemistry*, vol. 424, pp. 27-30, 2009, reported production of CPD from 1,3-pentadiene, n-pentene, and an n-pentane. Yields to CPD were as high as 53%, 35%, and 21% for the conversion of 1,3-pentadiene, n-pentene, and an n-pentane respectively at 600° C. on 2% $Pt/SiO_2$. While initial production of CPD was observed, drastic catalyst deactivation within the first minutes of the reaction was observed. Experiments conducted on Pt-containing silica show moderate conversion of n-pentane over $Pt—Sn/SiO_2$, but with poor selectivity and yield to cyclic $C_5$ products. The use of $H_2S$ as a 1,3-pentadiene cyclization promoter was presented by Fel'dblyum, infra, as well as in Marcinkowski, "Isomerization and Dehydrogenation of 1,3-Pentadiene," M.S., University of Central Florida, 1977. Marcinkowski showed 80% conversion of 1,3,-pentadiene with 80% selectivity to CPD with $H_2S$ at 700° C. High temperature, limited feedstock, and potential of products containing sulfur that would later need scrubbing make this process undesirable.

López et al. in "n-Pentane Hydroisomerization on Pt Containing HZSM-5, HBEA, and SAPO-11," *Catalysis Letters*, vol. 122, pp. 267-273, 2008, studied reactions of n-pentane on Pt-containing zeolites including H-ZSM-5. At intermediate temperatures (250° C.-400° C.), they reported efficient hydroisomerization of n-pentane on the Pt-zeolites with no discussion of cyclopentene formation. It is desirable to avoid this deleterious chemistry as branched $C_5$ do not produce cyclic $C_5$ as efficiently as linear $C_5$, as discussed above.

Li et al. in "Catalytic dehydroisomerization of n-alkanes to isoalkenes," *Journal of Catalysis*, vol. 255, pp. 134-137, 2008, also studied n-pentane dehydrogenation on Pt-containing zeolites in which Al had been isomorphically substituted with Fe. These Pt/[Fe]ZSM-5 catalysts were efficient dehydrogenating and isomerizing n-pentane, but under the reaction conditions used, no cyclic $C_5$ were produced and undesirable skeletal isomerization occurred.

U.S. Pat. No. 5,633,421 discloses a process for dehydrogenating $C_2$-$C_5$ paraffins to obtain corresponding olefins. Similarly, U.S. Pat. No. 2,982,798 discloses a process for dehydrogenating an aliphatic hydrocarbon containing 3 to 6, inclusive, carbon atoms. However, neither U.S. Pat. No. 5,633,421 nor U.S. Pat. No. 2,982,798 disclose production of CPD from acyclic $C_5$ hydrocarbons, which are desirable as feedstock because they are plentiful and low cost.

Further, on-purpose production of CPD, propylene, ethylene, and benzene is accomplished via endothermic reactions. Engineering process and reactor design for catalyst driven endothermic reactions presents many challenges. For example, maintaining high temperatures required for the reactions including transferring a large amount of heat to a catalyst can be difficult. Production of CPD is especially difficult amongst endothermic processes because it is favored by low pressure and high temperature, but competing reactions such as cracking of n-pentane and other $C_5$ hydrocarbons can occur at relatively low temperature (e.g., 450° C.-500° C.).

Additional challenges may include loss of catalyst activity due to coking during the process and further processing needed to remove coke from the catalyst, and the inability to use oxygen-containing gas to directly provide the heat input necessary to counter the endothermic nature of the reaction without damaging the catalyst. Moreover, non-uniform catalyst aging can also occur, which can impact resulting product selectivity and catalyst life.

Furthermore, challenges exist in reactor design, especially with respect to material selection, since the reactions are carried out at higher temperatures and highly carburizing conditions. Metal alloys can potentially undergo carburization (resulting in loss in mechanical properties) as well as metal dusting (resulting in loss of metal via formation of metastable carbides) under the desired reaction conditions. Thus, given the need for large heat input to drive the reaction, presence of metallic heat-transfer surfaces exposed to the reaction mixture need to be capable of resisting attack via carburization/metal dusting.

Hence, there remains a need for a process to convert acyclic hydrocarbons to alkenes, cyclic hydrocarbons, and aromatics, particularly acyclic $C_5$ hydrocarbon to CPD, preferably at commercial rates and conditions. Further, there is a need for a catalytic process targeted for the production of CPD, which generates CPD in high yield from plentiful $C_5$ feedstocks without excessive production of $C_{4-}$ cracked products and with acceptable catalyst aging properties. Additionally, there is a need for processes and systems for on-purpose production of CPD, propylene, ethylene, and benzene from acyclic hydrocarbons, which addresses the above-described challenges.

SUMMARY OF THE INVENTION

In one aspect, this invention relates to a process for converting acyclic hydrocarbons to alkenes, cyclic hydrocarbons, and/or aromatics in a reactor system, wherein the process comprises: heating an electrically-conductive reaction zone by applying an electrical current to the electrically-conductive reaction zone; and contacting a feedstock comprising acyclic hydrocarbons with a catalyst material in the electrically-conductive reaction zone under reaction conditions to convert at least a portion of the acyclic hydrocarbons to an effluent comprising alkenes, cyclic hydrocarbons, and/or aromatics, wherein the catalyst material is present within and/or at least partially coated on an interior channel of the electrically-conductive reaction zone.

In another aspect, this invention also relates to a reaction system adapted for converting acyclic hydrocarbons to alkenes, cyclic hydrocarbons, and/or aromatics, wherein the reaction system comprises: a feedstock stream comprising acyclic hydrocarbons; an effluent stream comprising alkenes, cyclic hydrocarbons, and/or aromatics; and one or more electrically-conductive reaction zones operated under reaction conditions to convert at least a portion of the acyclic hydrocarbons to alkenes, cyclic hydrocarbons, and/or aromatics, wherein the one or more electrically-conductive reaction zones each independently comprises: catalyst material present within and/or at least partially coated on an interior channel of the electrically-conductive reaction zone; a feedstock stream inlet; an effluent stream outlet; and a means for applying an electrical current to the electrically-conductive reaction zone.

BRIEF DESCRIPTION OF THE FIGURES

Corresponding reference numerals indicate corresponding parts throughout the several views of the drawings.

DETAILED DESCRIPTION OF THE INVENTION

Figure 1:
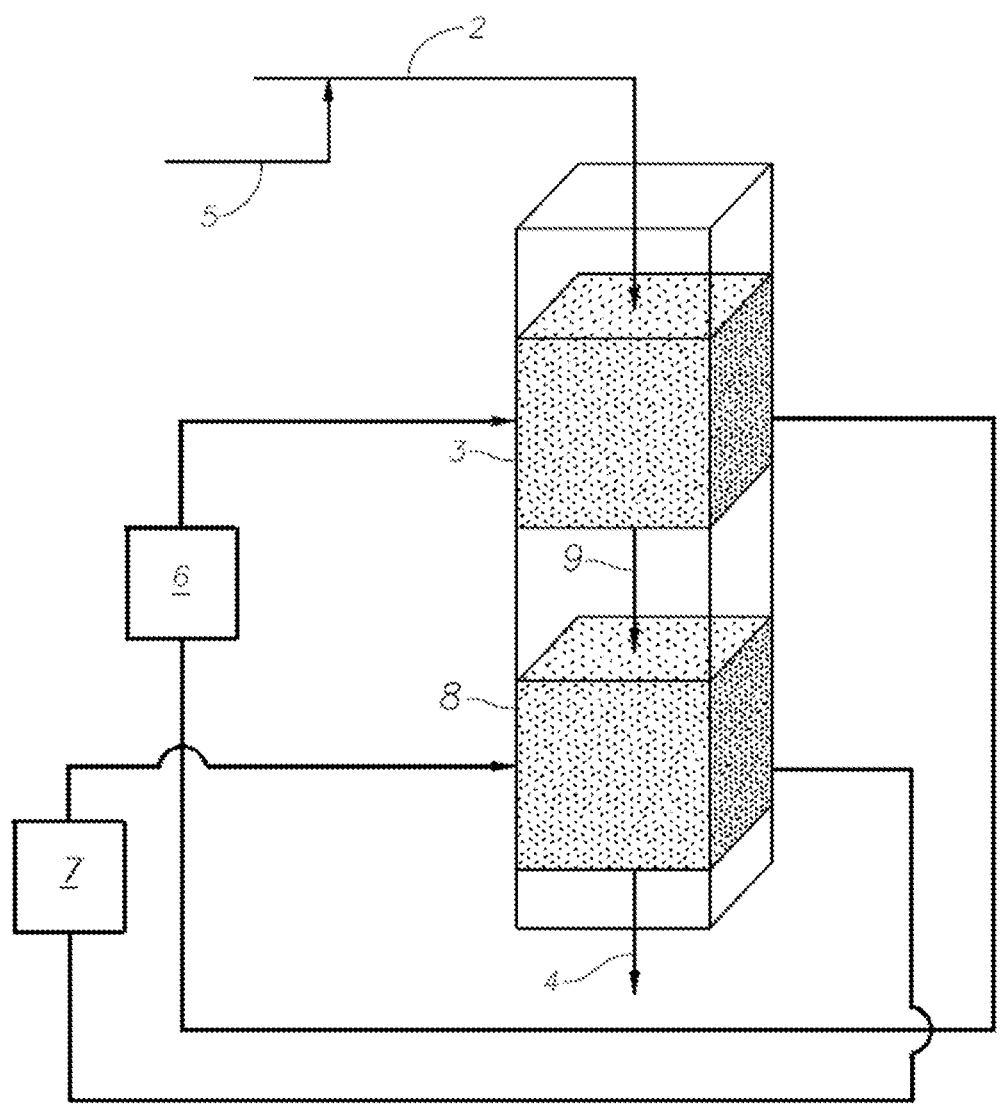
FIG. 1 is a diagram of a reactor system according to an embodiment of the invention.

All numerical values within the detailed description and the claims herein are modified by "about" or "approximately" the indicated value, and Lake into account experimental error and variations that would be expected by a person having ordinary skill in the art. Unless otherwise indicated, room temperature is 23° C.

I. Definitions

To facilitate an understanding of the present invention, a number of terms and phrases are defined below.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A", and "B."

As used herein, the term "about" refers to a range of values of plus or minus 10% of a specified value. For example, the phrase "200" includes plus or minus 10% of 200, or from 180 to 220.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n. The term "$C_n$" means hydrocarbon(s) having n carbon atom(s) per molecule, wherein n is a positive integer.

As used herein, the term "light hydrocarbon" means light paraffinic and/or olefinic hydrocarbons comprised substantially of hydrogen and carbon only and has one to no more than 4 carbon atoms.

The term "saturates" includes, but is not limited to, alkanes and cycloalkanes.

The term "non-saturates" includes, but is not limited to, alkenes, dialkenes, alkynes, cyclo-alkenes, and cyclo-dialkenes.

The term "cyclic hydrocarbon" denotes groups such as the cyclopropane, cyclopropene, cyclobutane, cyclobutadiene etc., and substituted analogues of these structures. These cyclic hydrocarbons can be single- or multi-ring structures.

The term "cyclics $C_5$" or "$cC_5$" includes, but is not limited to, cyclopentane, cyclopentene, cyclopentadiene, and mixtures of two or more thereof. The term "cyclic $C_5$" or "$cC_5$" also includes alkylated analogs of any of the foregoing, e.g., methyl cyclopentane, methyl cyclopentene, and methyl cyclopentadiene. It should be recognized for purposes of the invention that cyclopentadiene spontaneously dimerizes over time to form dicyclopentadiene via Diels-Alder condensation over a range of conditions, including ambient temperature and pressure.

The term "acyclics" includes, but is not limited to, linear and branched saturates and non-saturates.

The term "alkane" refers to non-aromatic saturated hydrocarbons with the general formula $C_6H_{(2n+2)}$, where n is 1 or greater. An alkane may be straight chained or branched. Examples of alkanes include, but are not limited to methane, ethane, propane, butane, pentane, hexane, heptane and octane. "Alkane" is intended to embrace all structural isomeric forms of an alkane. For example, butane encompasses n-butane and isobutane; pentane encompasses n-pentane, isopentane and neopentane.

The term "alkene," alternatively referred to as "olefin," refers to a branched or unbranched unsaturated hydrocarbon having one or more carbon-carbon double bonds. A simple alkene comprises the general formula $C_nH_{2n}$, where n is 2 or greater. Examples of alkenes include, but are not limited to ethylene, propylene, butylene, pentene, hexene and heptene. "Alkene" is intended to embrace all structural isomeric forms of an alkene. For example, butylene encompasses but-1-ene, (Z)-but-2-ene, etc.

The term "aromatic" means a planar cyclic hydrocarbyl with conjugated double bonds, such as benzene. As used herein, the term aromatic encompasses compounds containing one or more aromatic rings, including, but not limited to, benzene, toluene, and xylene, and polynuclear aromatics (PNAs), which include naphthalene, anthracene, chrysene, and their alkylated versions. The term "$C_{6+}$ aromatics" includes compounds based upon an aromatic ring having six or more ring atoms, including, but not limited to, benzene, toluene, and xylene, and polynuclear aromatics (PNAs), which include naphthalene, anthracene, chrysene, and their alkylated versions.

The term "BTX" includes, but is not limited to, a mixture of benzene, toluene, and xylene (ortho and/or meta and/or para).

The term "coke" includes, but is not limited to, a low hydrogen content hydrocarbon that is adsorbed on the catalyst composition.

The term "$C_{n+}$" means hydrocarbon(s) having at least n carbon atom(s) per molecule.

The term "$C_{n-}$" means hydrocarbon(s) having no more than n carbon atom(s) per molecule.

The term "$C_5$ feedstock" includes a feedstock containing n-pentane, such as a feedstock which is predominately normal pentane and isopentane (also referred to as methylbutane), with smaller fractions of cyclopentane and neopentane (also referred to as 2,2-dimethylpropane).

All numbers and references to the Periodic Table of Elements are based on the new notation as set out in Chemical and Engineering News, 63(5), 27 (1985), unless otherwise specified.

The term "Group 10 metal" means an element in Group 10 of the Periodic Table and includes, but is not limited to, Ni, Pd, and Pt, and a mixture of two or more thereof.

The term "Group 11 metal" means an element in Group 11 of the Periodic Table and includes, but is not limited to, Cu, Ag, Au, and a mixture of two or more thereof.

The term "Group 1 alkali metal" means an element in Group 1 of the Periodic Table and includes, but is not limited to, Li, Na, K, Rb, Cs, and a mixture of two or more thereof, and excludes hydrogen.

The term "Group 2 alkaline earth metal" means an element in Group 2 of the Periodic Table and includes, but is not limited to, Be, Mg, Ca, Sr, Ba, and a mixture of two or more thereof.

The term "rare earth metal" means an element in the Lanthanide series of the Periodic Table, as well as scandium and yttrium. The term rare earth metal includes, but is not limited to, lanthanum, praseodymium, neodymium, cerium, yttrium, and a mixture of two or more thereof.

The term "oxygen" includes air, $O_2$, $H_2O$, CO, and $CO_2$.

The term "constraint index" is defined in U.S. Pat. Nos. 3,972,832 and 4,016,218, both of which are incorporated herein by reference.

As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms, which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding of at least two monolayers of one unit cell thickness. The stacking of such second degree building blocks may be in a regular fashion, an irregular fashion, a random fashion, or any combination thereof; and molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

As used herein, the term "molecular sieve" is used synonymously with the term "microporous crystalline material" or "zeolite."

As used herein, the term "selectivity" means the moles of carbon in the respective cyclic $C_5$, CPD, $C_1$, and $C_{2-4}$ formed divided by total moles of carbon in the pentane converted. For example, the term "carbon selectivity to cyclic $C_5$ of at least 30%" means that at least 30 moles of carbon in the cyclic $C_5$ is formed per 100 moles of carbon in the pentane converted.

As used herein, the term "conversion" means the moles of carbon in the acyclic $C_5$ feedstock that is converted to a product. The phrase "a conversion of at least 70% of said acyclic $C_5$ feedstock to said product" means that at least 70% of the moles of said acyclic $C_5$ feedstock was converted to a product.

As used herein, the term "Alpha Value" is used as a measure of the cracking activity of a catalyst and is described in U.S. Pat. No. 3,354,078 and in the Journal of Catalysis, Vol. 4, p. 527 (1965); Vol. 6, p. 278, (1966) and Vol. 61, p. 395, (1980), each incorporated herein by reference. The experimental conditions of the test used herein included a constant temperature of 538° C. and a variable flow rate as described in detail in the Journal of Catalysis, Vol. 61, p. 395, (1980).

As used herein, the term "monolith" refers to a structure containing a multitude of interior channels, preferably arranged in parallel, in a uniform block of material.

As used herein, the term "reactor system" refers to a system including one or more reactors and all necessary and optional equipment used in the production of cyclopentadiene.

As used herein, the term "reactor" refers to any vessel(s) in which a chemical reaction occurs. Reactor includes both distinct reactors, as well as reaction zones within a single reactor apparatus and, as applicable, reactions zones across multiple reactors. In other words, and as is common, a single reactor may have multiple reaction zones. Where the description refers to a first and second reactor, the person of ordinary skill in the art will readily recognize such reference includes two reactors, as well as a single reactor vessel having first and second reaction zones. Likewise, a first reactor effluent and a second reactor effluent will be recognized to include the effluent from the first reaction zone and the second reaction zone of a single reactor, respectively.

A reactor/reaction zone may be an adiabatic reactor/reaction zone or a diabatic reactor/reaction zone. As used herein, the term "adiabatic" refers to a reaction zone for which there is essentially no heat input into the system other than by a flowing process fluid. A reaction zone that has unavoidable losses due to conduction and/or radiation may also be considered adiabatic for the purpose of this invention. As used herein, the term "diabatic" refers to a reactor/reaction zone to which heat is supplied by a means in addition to that provided by the flowing process fluid.

For purposes of the invention, 1 psi is equivalent to 6.895 kPa. Particularly, 1 psia is equivalent to 1 kPa absolute (kPa-a). Likewise, 1 psig is equivalent to 6.895 kPa gauge (kPa-g).

II. Acyclic Hydrocarbon Conversion Process

In a first aspect, this invention relates to a process for converting acyclic hydrocarbons to alkenes, cyclic hydrocarbons and/or aromatics in a reactor system. The process may comprise contacting a feedstock comprising acyclic hydrocarbons with a catalyst material in an electrically-conductive reaction zone under reaction conditions to convert at least a portion of the acyclic hydrocarbons to an effluent comprising alkenes, cyclic hydrocarbons, and/or aromatics and heating the electrically-conductive reaction zone by applying an electrical current to the electrically-conductive reaction zone. In various aspects, the catalyst material may be present within and/or at least partially coated on an interior channel of the electrically-conductive reaction zone In one or more embodiments, this invention relates to a process for conversion of an acyclic $C_5$ feedstock to a product comprising cyclic $C_5$ compounds (e.g., cyclopentadiene). The process comprising the steps of contacting said feedstock and, optionally, hydrogen under acyclic $C_5$ conversion conditions in the presence of one or more catalyst compositions, including but not limited to the catalyst compositions described herein, to form said product.

In one or more embodiments, the product of the process for conversion of an acyclic $C_5$ feedstock comprises cyclic $C_5$ compounds. The cyclic $C_5$ compounds comprise one or more of cyclopentane, cyclopentene, cyclopentadiene, and includes mixtures thereof. In one or more embodiments, the cyclic $C_5$ compounds comprise at least 20 wt %, or 30 wt %, or 40 wt %, or 70 wt % cyclopentadiene, or in the range of from 10 wt % to 80 wt %, alternately 20 wt % to 70 wt %.

In one or more embodiments, the acyclic $C_5$ conversion conditions include at least a temperature, an n-pentane partial pressure, and a weight hourly space velocity (WHSV). The temperature is in the range of 400° C. to 700° C., or in the range from 450° C. to 650° C., preferably, in the range from 500° C. to 600° C. The n-pentane partial pressure is in the range of 3 to 100 psia at the reactor inlet, or in the range from 3 to 50 psia, preferably, in the range from 3 psia to 20 psia. The weight hourly space velocity is in the range from 1 to 50 $hr^{-1}$, or in the range from 1 to 20 $hr^{-1}$. Such conditions include a molar ratio of the optional hydrogen co-feed to the acyclic $C_5$ feedstock in the range of 0 to 3, or in the range from 1 to 2. Such conditions may also include co-feed $C_1$-$C_4$ hydrocarbons with the acyclic $C_5$ feed.

In one or more embodiments, this invention relates to a process for conversion of n-pentane to cyclopentadiene comprising the steps of contacting n-pentane and, optionally, hydrogen (if present, typically $H_2$ is present at a ratio to n-pentane of 0.01 to 3.0) with one or more catalyst compositions, including but not limited to the catalyst compositions described herein and the inert materials described herein, to form cyclopentadiene at a temperature of 400° C. to 700° C., an n-pentane partial pressure of 3 to 100 psia at the reactor inlet, and a weight hourly space velocity of 1 to 50 $hr^{-1}$.

A. Reaction Step
  i. Feedstock

During a reaction step of the process, a feedstock comprising acyclic hydrocarbons, preferably acyclic $C_2$-$C_{10}$ hydrocarbons are provided to an electrically conductive reaction zone. Acyclic $C_2$-$C_{10}$ hydrocarbons include, but are not limited to alkanes (e.g., ethane, propane, butane, pentane, hexane, etc.), alkenes (e.g., ethylene, propylene, butylene, etc.), alkynes (e.g., ethyne, propyne, 1-butyne, 2-butyne, etc.), dialkenes (e.g., 1,2-propadiene, 1,3-butadiene, 1,3-pentadiene, etc.) and combinations thereof. An acyclic $C_2$-$C_8$ hydrocarbon feedstock, useful herein, is obtainable from crude oil or natural gas condensate. Optionally, hydrogen may be present in the feedstock as well. The molar ratio of optional hydrogen to acyclic hydrocarbon is preferably between 0 to 3, or in the range of 1 to 2. Hydrogen may be included in the feedstock in order to minimize production of coke material on the particulate material and/or to fluidize the particulate material in the one or more reaction zones.

In various aspects, the feedstock may preferably be an acyclic $C_5$ feedstock and can include cracked $C_5$ (in various degrees of unsaturation: alkenes, dialkenes, alkynes) produced by refining and chemical processes, such as fluid catalytic cracking (FCC), reforming, hydrocracking, hydrotreating, coking, and steam cracking.

Preferably, in one or more embodiments, the acyclic $C_5$ feedstock comprises at least 50 wt %, or 60 wt %, or 75 wt %, or 90 wt % acyclic hydrocarbons, or in the range from 50 wt % to 100 wt % n-pentane. Preferably, an amount of the acyclic hydrocarbons in the feedstock converted to alkenes (e.g., propylene), cyclic hydrocarbons (e.g., cyclopentadiene) and/or aromatics (e.g., benzene) is ≥5.0 wt %, ≥10.0 wt %, ≥20.0 wt %, ≥30.0 wt %, ≥40.0 wt %, ≥50.0 wt %, ≥60.0 wt %, ≥70.0 wt %, ≥80.0 wt %, or ≥90.0 wt %.

In one or more embodiments, the acyclic $C_5$ feedstock useful in the process of this invention comprises pentane, pentene, pentadiene and mixtures of two or more thereof. Preferably, in one or more embodiments, the acyclic $C_5$ feedstock comprises at least 50 wt %, or 60 wt %, or 75 wt %, or 90 wt % n-pentane, or in the range from 50 wt % to 100 wt % n-pentane. Preferably, an amount of the acyclic hydrocarbons in the feedstock converted to alkenes (e.g., propylene), cyclic hydrocarbons (e.g., cyclopentadiene) and/or aromatics (e.g., benzene) is ≥5.0 wt %, ≥10.0 wt %, ≥20.0 wt %, ≥30.0 wt %, ≥40.0 wt %, ≥50.0 wt %, ≥60.0 wt %, ≥70.0 wt %, ≥80.0 wt %, or ≥90.0 wt %.

The acyclic hydrocarbon feedstock optionally does not comprise $C_6$ aromatic compounds, such as benzene. Preferably $C_6$ aromatic compounds are present at less than 5 wt %, preferably less than 1 wt %, preferably less than 0.01 wt %, and preferably at zero wt %. Additionally or alternatively, the acyclic hydrocarbon feedstock optionally does not comprise benzene, toluene, or xylene (ortho, meta, or para). Preferably any benzene, toluene, or xylene (ortho, meta, or para) compounds are present at less than 5 wt %, preferably less than 1 wt %, preferably less than 0.01 wt %, and preferably at zero wt %.

The acyclic hydrocarbon feedstock optionally does not comprise $C_{6+}$ aromatic compounds. Preferably $C_{6+}$ aromatic compounds are present at less than 5 wt %, preferably less than 1 wt %, preferably less than 0.01 wt %, and preferably at zero wt %.

Preferably, an amount of the $C_5$ hydrocarbons (e.g., acyclic $C_5$ hydrocarbons) in the feedstock converted to cyclopentadiene is ≥5.0 wt %, ≥10.0 wt %, ≥20.0 wt %, ≥30.0 wt %, ≥40.0 wt %, ≥50.0 wt %, ≥60.0 wt %, ≥70.0 wt %, ≥80.0 wt %, or ≥90.0 wt %. Preferably, at least 30.0 wt % or at least 60.0 wt % of the $C_5$ hydrocarbons (e.g., acyclic $C_5$ hydrocarbons) is converted to cyclopentadiene. Ranges expressly disclosed include combinations of any of the above-enumerated values; e.g., 5.0% to 90.0 wt %, 10.0 wt % to 80.0 wt %, 20.0 wt % to 70.0 wt %, 20.0 wt % to 60.0 wt %, etc. Preferably, 20.0 wt % to 90.0 wt % of the $C_5$ hydrocarbons (e.g., acyclic $C_5$ hydrocarbons) is converted to cyclopentadiene, more preferably 30.0 wt % to 85.0 wt %, more preferably 40.0 wt % to 80.0 wt %, more preferably 45.0 wt % to 75.0 wt %, and more preferably 50.0 wt % to 70.0 wt %.

Preferably, a hydrogen co-feedstock comprising hydrogen and, optionally, light hydrocarbons, such as $C_1$-$C_4$ hydrocarbons, is also fed into an electrically conductive reaction zone. Preferably, at least a portion of the hydrogen co-feedstock is admixed with the feedstock prior to being fed into the reaction zone. The presence of hydrogen in the feed mixture at the inlet location, where the feed first comes into contact with the catalyst, prevents or reduces the formation of coke on the catalyst particles. In another embodiment, $C_1$-$C_4$ hydrocarbons may also be co-fed with feedstock.

ii. Electrically-Conductive Reaction Zone

The feedstock is fed into at an electrically-conductive reaction zone (e.g. a first electrically-conductive reaction zone) and contacted with a catalyst material therein under reaction conditions to convert at least a portion of the acyclic hydrocarbons (e.g., acyclic $C_5$ hydrocarbons) to an effluent (e.g., a first effluent) comprising alkenes (e.g., propylene), cyclic hydrocarbons (e.g., cyclopentadiene) and aromatics (e.g., benzene). The reaction system may comprise at least a first electrically-conductive reaction zone, a second electrically-conductive reaction zone, a third electrically-conductive reaction zone, a fourth electrically-conductive reaction zone, a fifth electrically-conductive reaction zone, a sixth electrically-conductive reaction zone, a seventh electrically-conductive reaction zone, and/or an eighth electrically-conductive reaction zone, etc. As understood herein, each electrically-conductive reaction zone may be an individual reactor (e.g., a fixed bed reactor) or a reactor may comprise one or more of the electrically-conductive reaction zones.

An electrically-conductive reaction zone may include at least one internal structure to support catalyst material, to distribute feedstock uniformly, to collect hydrocarbon product, and/or reduce pressure drop within the reaction zone. For example, an electrically-conductive reaction zone may include at least one internal structure, preferably a plurality of internal structures (e.g., 2, 3, 4, 5, 6, 7, 8, 9, 10, 15, 20, 30, 40, 50, etc.). Examples of suitable internal structures include a plurality of support grids, hold down grids, shells, baffles, sheds, trays, tubes, rods, and/or distributors.

Each electrically-conductive reaction zone (e.g., first electrically-conductive reaction zone, second electrically-conductive reaction zone, third electrically-conductive reaction zone, etc.) independently may be a monolith, such as a honeycomb monolith, of any suitable geometry, preferably a rectangular cuboid. Generally, each electrically-conductive zone is comprised of any suitable electrically-conductive material, such as a ceramic material or a metallic material. Suitable ceramic materials include but are not limited to silicon carbide, aluminum nitride, boron nitride, tungsten carbide, a MAX phase alloy, a ferrochrome alloy and combinations thereof. As used herein, "MAX phase alloy" refers to a material having the formula, $M_{n+1}AX_n$, wherein M may be a transition metal; A may be a Group 13 element, a Group 14 element (according to the IUPAC periodic table), Cd, N, P, As or S; X may be C, N or B and n may be 1-3. In various aspects, M may be Sc, Ti, Zr, Hf, V, Nb, Ta, Cr and/or Mo; A may be Cd, Al, Ga, In, Tl, Si Ge, Sn, Pb, As, or S; and X may be N or C. Examples of MAX phase alloys include, but are not limited to $Ti_2CdC$, $Sc_2InC$, $Ti_2AlC$, $Ti_2GaC$, $Ti_2InC$, $Ti_2TlC$, $V_2AlC$, $V_2GaC$, $Cr_2GaC$, $Ti_2AlN$, $Ti_2GaN$, $Ti_2InN$, $V_2GaN$, $Cr_2GaN$, $Ti_2GeC$, $Ti_2SnC$, $Ti_2PbC$, $V_2GeC$, $Cr_2AlC$, $Cr_2GeC$, $V_2PC$, $V_2AsC$, $Ti_2SC$, $Zr_2InC$, $Zr_2TlC$, $Nb_2AlC$, $Nb_2GaC$, $Nb_2InC$, $Mo_2GaC$, $Zr_2InN$, $Zr_2TlN$, $Zr_2SnC$, $Zr_2PbC$, $Nb_2SnC$, $Nb_2PC$, $Nb_2AsC$, $Zr_2SC$, $Nb_2SC$, $Hf_2InC$, $Hf_2TlC$, $Ta_2AlC$, $Ta_2GaC$, $Hf_2SnC$, $Hf_2PbC$, $Hf_2SnN$, $Hf_2SC$, $Ti_3AlC_2$, $V_3AlC_2$, $Ti_3SiC_2$, $Ti_3GeC_2$, $Ti_3SnC_2$, $Ta_3AlC_2$, $Ti_4AlN_3$ $V_4AlC_3$, $Ti_4GaC_3$, $Ti_4SiC_3$, $Ti_4GeC_3$, $Nb_4AlC_3$, and $Ta_4AlC_3$. In particular, the electrically-conductive reaction zone (e.g. a first electrically-conductive reaction zone) may be a monolith reactor formed of silicon carbide.

The electrically-conductive reaction zone (e.g., first electrically-conductive reaction zone, second electrically-conductive reaction zone, third electrically-conductive reaction zone, etc.) may further comprise two or more electrodes configured to pass current in a direction either parallel or perpendicular to reactant flow within the reaction zone, preferably in a direction perpendicular to reactant flow.

The electrically-conductive reaction zone (e.g., first electrically-conductive reaction zone, second electrically-conductive reaction zone, third electrically-conductive reaction zone, etc.) may further comprise a catalyst material (as further described herein) within and/or at least partially coated on an interior channel of an electrically-conductive reaction zone. In various aspects, application of the catalyst material may be performed during manufacture of the electrically-conductive reaction zone. For example, in various aspects a slurry containing the catalyst material may be extruded to form the electrically-conductive reaction zone. Alternatively or additionally, the catalyst material may be applied on an interior channel of the electrically-conductive zone post-manufacture via any suitable method, e.g., wash-coating, spray-coating, dip coating, impregnation, electrophoretic deposition, and/or chemical vapor deposition. The catalyst material may be present as a thin layer, for example, having a thickness of 5.0 µm to 1000 µm, 10 µm to 500 µm, or 50 µm to 300 µm, on an interior channel of the electrically-conductive zone. As discussed above, on-purpose production of CPD, propylene, ethylene, and benzene is accomplished via endothermic reactions, which present various challenges, such as maintaining high temperatures required for the reactions including transferring a large amount of heat to a catalyst). Advantageously, endothermic heat of reaction may be provided by applying an electrical current to the electrically-conductive reaction zone (e.g. first electrically-conductive reaction zone, second electrically-conductive reaction zone, third electrically-conductive reaction zone, etc.). The electrical current may be applied via any suitable means. For example, the power required for electrical heating of the electrically-conductive reaction zone can be provided via electricity generated on-site via gas turbine. In other words, the catalyst material present within and/or at least partially coated on an interior channel of the electrically-conductive reaction zone may be heated via resistive heating of the underlying electrically-conductive reaction zone. Thus, heat may be advantageously released in a substantially uniform manner throughout the electrically-conductive reaction zone based on the resistivity of the electrically-conductive reaction zone (e.g., ceramic monolith) and applied power or electrical current. Uniform heat release in the electrically-conductive reaction zone can minimize undesirable temperature gradients and reduce non-uniformity in catalyst ageing. Furthermore, an axial temperature profile in an electrically-conductive reaction zone can be controlled by varying the applied electrical current or power to the electrically-conductive reaction zone. In particular, the electrical current may be provided in a substantially orthogonal direction with respect to a direction of flow of the feedstock through the electrically-conductive reaction zone.

Optionally, the one or more reaction zones may include one or more heating devices in order to maintain a temperature therein. Examples of suitable heating devices known in the art include, but are not limited to a fired tube, a heated coil with a high temperature heat transfer fluid, an electrical heater, and/or a microwave emitter. As used herein, "coil" refers to a structure placed within a vessel through which a heat transfer fluid flows to transfer heat to the vessel contents. A coil may have any suitable cross-sectional shape and may be straight, include u-bends, include loops, etc.

Optionally, the heat exchanger tubes in one or more reaction zones may be coated or clad with a ceramic coating and/or carbide-forming metal (e.g., W, Mo) on the outer surface, exposed to the hydrocarbon reaction mixture, to provide carburization and metal dusting resistance as well as mitigating coking on the metal surface. Ceramic coatings may include metal carbides (e.g., tungsten carbide, chromium carbide, molybdenum carbide, etc.), metal carbide-metal composites (e.g., tungsten carbide-cobalt composite, tungsten carbide-Inconel 890 composite, etc.), metal oxides (e.g., mixed oxides of MCrAlY where M can be Co, Ni, Co/Ni, etc., aluminum oxide, yttria-stabilized zirconia, chromium oxide, titanium oxide, etc.). Carbide formers (e.g., tungsten metal, molybdenum metal, chromium metal, etc.)

under these highly carburizing conditions (high carbon activity and high temperature) form a stable metal carbide layer, thereby preventing further carbon ingress and carburization of the underlying metallurgy. These coatings may be applied via various methods known in the art, such as flame spraying, high velocity oxy-fuel (HVOF/HVAF), electric arc spray, plasma spray, cold spray, electrophoretic deposition, painting, laser cladding, twin wire arc, dip coating, etc.

In various aspects, the electrical current applied to an electrically-conductive reaction zone, may provide ≥10%, ≥20%, ≥25%, ≥30%, ≥35%, ≥40%≥45%, ≥50%, ≥55%, ≥60%, ≥65%, ≥70%, ≥75%, ≥80%, ≥85%, ≥90%, ≥95%, or 100% of the required heat for converting at least a portion of the acyclic hydrocarbons to the first effluent comprising alkenes, cyclic hydrocarbons and/or aromatics, particularly converting acyclic $C_5$ hydrocarbons to cyclopentadiene. In particular, the electrical current applied to an electrically-conductive reaction zone may provide ≥25% of the required heat for converting at least a portion of the acyclic $C_5$ hydrocarbons to the first effluent comprising cyclopentadiene. Ranges expressly disclosed include combinations of any of the above-enumerated values; e.g., 20% to 100%, 40% to 95%, 50% to 90%, etc. Preferably, the electrical current applied to an electrically-conductive reaction zone may provide 20% to 100% of the required heat, more preferably 40% to 100% of the required heat, or more preferably 50% to 100% of the required heat.

Preferably, the reactor system includes 1 to 50 electrically-conductive reaction zones, more preferably 1 to 40 electrically-conductive reaction zones, more preferably 10 to 40 electrically-conductive reaction zones. Where the reactor system includes two or more electrically-conductive reaction zones, the electrically-conductive reaction zones may be arranged in any suitable configuration, such as in series. Additionally or alternatively, the two or more reaction zones may be operated at independent temperatures. For example, a first electrically-conductive reaction zone, a second electrically-conductive reaction zone, and a third electrically-conductive reaction zone may be present and operated in parallel and/or series. Additionally or alternatively, a first electrically-conductive reaction zone, a second electrically-conductive reaction zone, and a third electrically-conductive reaction zone may be present and operated at independent temperatures.

In aspects where the reactor system includes two or more electrically-conductive reaction zones, the reactor system preferably includes two or more monoliths configured in parallel and/or series. For example, the reaction system may include one or more monolith units, wherein the term "monolith unit" refers to a configuration of from 1 to 50 monoliths in series, such as from 1 to 40 monoliths in series. Particularly preferably, the reaction system may comprise a network of monoliths, wherein the network comprises two or more monolith units in parallel. Optionally, each monolith unit may be housed in a separate reactor vessel.

During the reaction zone, an electrically-conductive reaction zone is operated under reaction conditions sufficient to convert at least a portion of the acyclic hydrocarbons feedstock, preferably acyclic $C_5$ hydrocarbons, to an effluent comprising alkene, cyclic hydrocarbons, and aromatics, preferably cyclopentadiene. Preferably, the feedstock (e.g., acyclic hydrocarbons) may be fed to the reaction system at a weight hourly space velocity (WHSV, mass of acyclic hydrocarbons/mass of catalyst/hour) in the range of from 1.0 to 1000.0 $hr^{-1}$. The WHSV may be 1.0 to 900.0 $hr^{-1}$, 1.0 to 800.0 $hr^{-1}$, 1.0 to 700.0 $hr^{-1}$, 1.0 to 600.0 $hr^-$, 1.0 to 500.0 $hr^{-1}$, 1.0 to 400.0 $hr^-$, 1.0 to 300.0 $hr^{-1}$, 1.0 to 200.0 $hr^-$, 1.0 to 100.0 $hr^{-1}$, 1.0 to 90.0 $hr^{-1}$, 1.0 to 80.0 $hr^{-1}$, 1.0 to 70.0 $hr^{-1}$, 1.0 to 60.0 $hr^{-1}$, 1.0 to 50.0 $hr^{-1}$, 1.0 to 40.0 $hr^{-1}$, 1.0 to 30.0 $hr^{-1}$, 1.0 to 20.0 $hr^{-1}$, 1.0 to 10.0 $hr^{-1}$, 1.0 to 5.0 $hr^{-1}$, 2.0 to 1000.0 $hr^{-1}$, 2.0 to 900.0 $hr^{-1}$, 2.0 to 800.0 $hr^{-1}$, 2.0 to 700.0 $hr^{-1}$, 2.0 to 600.0 $hr^{-1}$, 2.0 to 500.0 $hr^{-1}$, 2.0 to 400.0 $hr^{-1}$, 2.0 to 300.0 $hr^{-1}$, 2.0 to 200.0 $hr^{-1}$, 2.0 to 100.0 $hr^{-1}$, 2.0 to 90.0 $hr^{-1}$, 2.0 to 80.0 $hr^{-1}$, 2.0 to 70.0 $hr^{-1}$, 2.0 to 60.0 $hr^{-1}$, 2.0 to 50.0 $hr^{-1}$, 2.0 to 40.0 $hr^{-1}$, 2.0 to 30.0 $hr^{-1}$, 2.0 to 20.0 $hr^{-1}$, 2.0 to 10.0 $hr^{-1}$, and 2.0 to 5.0 $hr^{-1}$. Preferably, the WHSV is 1.0 to 100.0 $hr^{-1}$, more preferably 1.0 to 60.0 $hr^{-1}$, more preferably 2.0 to 40.0 $hr^{-1}$, more preferably 2.0 to 20.0 $hr^{-1}$.

Additionally, it may be preferable that an isothermal or substantially isothermal temperature profile be maintained in an electrically-conductive reaction zone. A substantially isothermal temperature profile has the advantages of maximizing the effective utilization of the catalyst and minimizing the production of undesirable $C_{4-}$ byproducts. As used herein, "isothermal temperature profile" means that the temperature at each point within the reaction zone between the reactor inlet and reactor outlet as measured along the tube centerline of the reactor is kept essentially constant, e.g., at the same temperature or within the same narrow temperature range wherein the difference between an upper temperature and a lower temperature is no more than 40° C.; more preferably no more than 20° C. Preferably, the isothermal temperature profile is one where the temperature along the length of the reaction zone(s) within the reactor does not vary by more than 40° C. as compared to the average temperature within the reactor, alternately not more than 20° C., alternately not more than 10° C., alternately not more than 5° C. Alternately, the isothermal temperature profile is one where the temperature along the length of the reaction zone(s) within the reactor is within 20% of the average temperature within the reactor, alternately within 10%, alternately within 5%, alternately within 1% of the average temperature within the reactor.

Thus, the temperature of the feedstock (e.g., acyclic hydrocarbons) entering the reactor system at a feedstock inlet may be ≤750° C., ≤725° C., ≤700° C., ≤675° C., ≤650° C., ≤625° C., ≤600° C., ≤575° C., ≤550° C., ≤525° C., ≤500° C., ≤475° C., ≤450° C., ≤425° C., ≤400° C., ≤375° C., ≤350° C., ≤325° C., ≤300° C., ≤275° C., ≤250° C., ≤225° C. or ≤200° C. Preferably, the temperature of the feedstock (e.g., acyclic hydrocarbons) entering the reactor system is ≤675° C., more preferably ≤650° C., or more preferably ≤625° C. Ranges of temperatures expressly disclosed include combinations of any of the above-enumerated values, e.g., 300° C. to 750° C., 350° C. to 700° C., 450° C. to 650° C., 475° C. to 600° C., etc. Preferably, the temperature of the feedstock (e.g., acyclic hydrocarbons) entering the reaction system is 300° C. to 750° C., more preferably 400° C. to 700° C., more preferably 400° C. to 700° C., and more preferably 450° C. to 600° C. Providing the feedstock (e.g., acyclic $C_5$ hydrocarbons) at the above-described temperatures may advantageously minimize undesirable cracking of the $C_5$ hydrocarbons (e.g., acyclic $C_5$ hydrocarbons) before they can react in the presence of the catalyst material. The feedstock may be heated, optionally in the presence a hydrogen co-feed, in a furnace to achieve the above-described temperatures before entering an electrically-conductive reaction zone.

Additionally, the temperature of an effluent exiting an electrically-conductive reaction zone at an effluent outlet may be ≥400° C., ≥425° C., ≥450° C., ≥475° C., ≥500° C., ≥525° C., ≥550° C., ≥575° C., ≥600° C., ≥625° C., ≥650° C., ≥675° C., or ≥700° C. Preferably, the temperature of an effluent exiting an electrically-conductive reaction zone is ≥550° C., more preferably ≥575° C., more preferably ≥600° C. Ranges of temperatures expressly disclosed include combinations of any of the above-enumerated values, e.g., 400° C. to 700° C., 475° C. to 675° C., 525° C. to 650° C., 550° C. to 600° C., etc. Preferably, the temperature of an effluent exiting the electrically-conductive reaction zone is 475° C. to 700° C., more preferably 500° C. to 650° C., more preferably 550° C. to 625° C.

Additionally or alternatively, reaction conditions in an electrically-conductive reaction zone may include a temperature of ≥300° C., ≥325° C., ≥350° C., ≥375° C., ≥400° C., ≥425° C., ≥450° C., ≥475° C., ≥500° C., ≥525° C., ≥550° C., ≥575° C., ≥600° C. ≥625° C., ≥650° C., ≥675° C., or ≥700° C. Ranges of temperatures expressly disclosed include combinations of any of the above-enumerated values, e.g., 300° C. to 700° C., 350° C. to 675° C., and 400° C. to 700° C., etc. Preferably, the temperature may be 350° C. to 700° C., more preferably 400° C. to 700° C., or more preferably 500° C. to 650° C. Optionally, an electrically-conductive reaction zone may include one or more heating devices in order to maintain a temperature therein. Examples of suitable heating devices known in the art include, but are not limited to a fired tube, a heated coil with a high temperature heat transfer fluid, an electrical heater, and/or a microwave emitter. As used herein, "coil" refers to a structure placed within a vessel through which a heat transfer fluid flows to transfer heat to the vessel contents. A coil may have any suitable cross-sectional shape and may be straight, include u-bends, include loops, etc.

Additionally or alternatively, reaction conditions in an electrically-conductive reaction zone may include a pressure (e.g., effluent outlet pressure) of ≥1.0 psia, ≥2.0 psia, ≥3.0 psia, ≥4.0 psia, ≥5.0 psia, ≥10.0 psia, ≥15.0 psia, ≥20.0 psia, ≥25.0 psia, ≥30.0 psia, ≥35.0 psia, ≥40.0 psia, ≥45.0 psia, ≥50.0 psia, ≥55.0 psia, ≥60.0 psia, ≥65.0 psia, ≥70.0 psia, ≥75.0 psia, ≥80.0 psia, ≥85.0 psia, ≥90.0 psia, ≥95.0 psia, ≥100.0 psia, ≥125.0 psia, ≥150.0 psia, ≥175.0 psia or 200 psia. Ranges and combinations of temperatures and pressures expressly disclosed include combinations of any of the above-enumerated values, e.g., 1.0 psia to 200.0 psia, 2.0 psia to 175.0 psia, 5.0 psia to 95.0 psia, etc. Preferably, the pressure may be 3.0 psia to 100.0 psia, more preferably 3.0 psia to 50.0 psia, more preferably 3.0 psia to 20.0 psia. In particular, the reaction conditions may comprise a temperature of 400° C. to 700° C. and a pressure of 3.0 psia to 100 psia.

Additionally or alternatively, a pressure substantially at a feedstock inlet and/or substantially at an effluent outlet may be ≥0.5 psia, ≥1.0 psia, ≥2.0 psia, ≥3.0 psia, ≥4.0 psia, ≥5.0 psia, ≥10.0 psia, ≥14.0 psia, ≥15.0, psia ≥20.0 psia, ≥24.0 psia, ≥25.0 psia, ≥30.0 psia, ≥35.0 psia, ≥40.0 psia, ≥45.0 psia, ≥50.0 psia or ≥55.0 psia, ≥60.0 psia, ≥65.0 psia, ≥70.0 psia, ≥75.0 psia, ≥80.0 psia, ≥85.0 psia, ≥90.0 psia, ≥95.0 psia, ≥100.0 psia, ≥125.0 psia, or ≥150.0 psia. As understood herein, "at a feedstock inlet," "at an inlet," "at an effluent outlet," and "at an outlet" includes the space in and substantially around the inlet and/or outlet. Additionally or alternatively, a pressure substantially at an inlet of a feedstock (e.g., acyclic $C_5$ hydrocarbons) and/or substantially at an outlet of an effluent may be ≤1.0 psia, ≤2.0 psia, ≤3.0 psia, ≤4.0 psia, ≤5.0 psia, ≤10.0 psia, ≤14.0 psia, ≤15.0 psia, ≤20.0 psia, ≤24.0 psia, ≤25.0 psia, ≤30.0 psia, ≤35.0 psia, ≤40.0 psia, ≤45.0 psia, ≤50.0 psia, ≤55.0 psia, ≤60.0 psia, ≤65.0 psia, ≤70.0 psia, ≤75.0 psia, ≤80.0 psia, ≤85.0 psia, ≤90.0 psia, ≤95.0 psia, ≤100.0 psia, ≤125.0 psia, ≤150.0 psia, ≤175.0 psia, or ≤200.0 psia. Ranges of pressures expressly disclosed include combinations of any of the above-enumerated values, e.g., 10 psia to 70.0 psia, 20.0 psia to 60.0 psia, 0.5 psia to 50.0 psia, 5.0 psia to 35.0 psia, 1.0 psia to 15.0 psia, etc. In particular, the pressure substantially at an inlet of a feedstock (inlet pressure) may be 1.0 psia to 70.0 psia, preferably 5.0 psia to 50.0 psia, more preferably 10 psia to 30.0 psia. The pressure substantially at an outlet of an effluent (outlet pressure) may be 1.0 psia to 70.0 psia, more preferably 5.0 psia to 50.0 psia, more preferably 5.0 psia to 30.0 psia, more preferably 10 psia to 30 psia.

Preferably, the pressure drop (or delta pressure) across an electrically-conductive reaction zone (pressure at feedstock inlet minus pressure at effluent outlet) is lower, e.g., at least 0.1 psi, at least 0.2 psi, at least 0.3 psi, at least 0.4 psi, at least 0.5 psi, at least 0.6 psi, at least 0.7 psi, at least 0.8 psi, at least 0.9 psi, at least 1.0 psi, at least 1.5 psi, at least 2.0 psi, at least 4.0 psi, at least 6.0 psi, at least 8.0 psi, at least 10.0 psi, at least 12.0 psi, at least 15.0 psi, at least 20.0 psi, at least 25 psi, or at least 30 psi. Additionally or alternatively, the pressure drop across an electrically-conductive reaction zone may be between 0.3 to 30.0 psi, more preferably 0.4 to 25.0 psi, more preferably 0.5 to 10 psi.

Additionally or alternatively, a stream comprising hydrogen may be fed to an electrically-conductive reaction zone. Such a stream comprising hydrogen may be introduced into an electrically-conductive reaction zone in order to minimize production of coke material on the particulate material and/or to fluidize the particulate material in the one or more reaction zones. Such a stream comprising hydrogen may contain light hydrocarbons (e.g., $C_1$-$C_4$); preferably the content of light hydrocarbons is less than 50 mol %, less than 40 mol %, less than 30 mol %, less than 20 mol %, less than 10 mol %, less than 5 mol %, less than 1 mol %. Preferably, the stream comprising hydrogen is substantially free of oxygen, e.g., less than 1.0 wt %, less than 0.1 wt %, less than 0.01 wt %, less than 0.001 wt %, less than 0.0001 wt %, less than 0.00001 wt %, etc.

iii. Particulate Material

The electrically-conductive reaction zone (e.g., first electrically-conductive reaction zone, second electrically-conductive reaction zone, third electrically-conductive reaction zone, etc.) may further comprise a particulate material comprising a catalyst material within and/or at least partially coated on an interior channel of an electrically-conductive reaction zone as described above. The catalyst material, also referred to as a "catalyst composition," is present in the reaction system for promoting conversion of at least a portion of the acyclic hydrocarbons to alkenes, cyclic hydrocarbons and aromatics, in particular conversion of acyclic $C_5$ hydrocarbons to cyclopentadiene.

Catalyst compositions useful herein include microporous crystalline metallosilicates, such as crystalline aluminosilicates, crystalline ferrosilicates, or other metal-containing crystalline silicates (such as those where the metal or metal-containing compound is dispersed within the crystalline silicate structure and may or may not be a part of the crystalline framework). Microporous crystalline metallosilicate framework types useful as catalyst compositions herein include, but are not limited to, MWW, MFI, LTL, MOR, BEA, TON, MTW, MTT, FER, MRE, MFS, MEL, DDR, EUO, and FAU.

Particularly suitable microporous metallosilicates for use herein, include those of framework type MWW, MFI, LTL, MOR, BEA, TON, MTW, MTT, FER, MRE, MFS, MEL, DDR, EUO, and FAU (such as zeolite beta, mordenite, faujasite, Zeolite L, ZSM-5, ZSM-11, ZSM-22, ZSM-23, ZSM-35, ZSM-48, ZSM-50, ZSM-57, ZSM-58, and MCM- 22 family materials) where one or more metals from groups 8, 11, and 13 of the Periodic Table of the Elements (preferably one or more of Fe, Cu, Ag, Au, B, Al, Ga, and/or In) are incorporated in the crystal structure during synthesis or impregnated post crystallization. It is recognized that a metallosilicate may have one of more metals present and, for example, a material may be referred to as a ferrosilicate, but it will most likely still contain small amounts of aluminum.

The microporous crystalline metallosilicates preferably have a constraint index of less than 12, alternately from 1 to 12, alternately from 3 to 12. Aluminosilicates useful herein have a constraint index of less than 12, such as 1 to 12, alternately 3 to 12, and include, but are not limited to Zeolite beta, mordenite, faujasite, Zeolite L, ZSM-5, ZSM-11, ZSM-22, ZSM-23, ZSM-35, ZSM-48, ZSM-50, ZSM-57, ZSM-58, MCM-22 family materials, and mixtures of two or more thereof. In a preferred embodiment, the crystalline aluminosilicate has a constraint index of 3 to 12 and is ZSM-5.

ZSM-5 is described in U.S. Pat. No. 3,702,886. ZSM-11 is described in U.S. Pat. No. 3,709,979. ZSM-22 is described in U.S. Pat. No. 5,336,478. ZSM-23 is described in U.S. Pat. No. 4,076,842. ZSM-35 is described in U.S. Pat. No. 4,016,245. ZSM-48 is described in U.S. Pat. No. 4,375,573. ZSM-50 is described in U.S. Pat. No. 4,640,829. ZSM-57 is described in U.S. Pat. No. 4,873,067. ZSM-58 is described in U.S. Pat. No. 4,698,217.

The MCM-22 family material is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30, and mixtures of two or more thereof.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0 293 032), ITQ-1 (described in U.S. Pat. No. 6,077,498), and ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697), and mixtures of two or more thereof. Related zeolites to be included in the MCM-22 family are UZM-8 (described in U.S. Pat. No. 6,756,030) and UZM-8HS (described in U.S. Pat. No. 7,713,513), both of which are also suitable for use as the molecular sieve of the MCM-22 family In one or more embodiments, the crystalline metallosilicate has an Si/M molar ratio (where M is a group 8, 11, or 13 metal) greater than 3, or greater than 25, or greater than 50, or greater than 100, or greater than 400, or in the range from 100 to 2,000, or from 100 to 1,500, or from 50 to 2,000, or from 50 to 1,200.

In one or more embodiments, the crystalline aluminosilicate has an $SiO_2/Al_2O_3$ molar ratio greater than 3, or greater than 25, or greater than 50, or greater than 100, or greater than 400, or greater than 1,000, or in the range from 100 to 400, or from 100 to 500, or from 25 to 2,000, or from 50 to 1,500, or from 100 to 1,200, or from 50 to 1,000.

Typically, the microporous crystalline metallosilicate (such as an aluminosilicate) is combined with a Group 10 metal or metal compound and, optionally, one, two, three, or more additional metals selected from Groups 8, 9, 11, and 13 of the Periodic Table of the Elements and the rare earth metals, such as Ga, In, Zn, Cu, Re, Mo, W, La, Fe, Ag, Rh, Pr, La, and/or oxides, sulfides, nitrides, and/or carbides of these metals. Alternatively or additionally, the Group 10 metal is present in combination with a Group I alkali metal and/or a Group 2 alkaline earth metal.

In one or more embodiments, the Group 10 metal includes, or is selected from the group consisting of, Ni, Pd, and Pt, preferably Pt. The Group 10 metal content of said catalyst composition is at least 0.005 wt %, based on the weight of the catalyst composition. In one or more embodiments, the Group 10 content is in the range from 0.005 wt % to 10 wt %, or from 0.005 wt % up to 1.5 wt %, based on the weight of the catalyst composition.

The Group 1 alkali metal is generally present as an oxide and the metal is selected from the group consisting of lithium, sodium, potassium, rubidium, cesium, and mixtures of two or more thereof. The Group 2 alkaline earth metal is generally present as an oxide and the metal is selected from the group consisting of beryllium, magnesium, calcium, strontium, barium, and mixtures of two or more thereof.

In one or more embodiments, the Group 11 metal includes, or is selected from the group consisting of, silver, gold, copper, preferably silver or copper. The Group 11 metal content of said catalyst composition is at least 0.005 wt %, based on the weight of the catalyst composition. In one or more embodiments, the Group 11 content is in the range from 0.005 wt % to 10 wt %, or from 0.005 wt % up to 1.5 wt %, based on the weight of the catalyst composition. In one or more embodiments, the molar ratio of said Group 11 metal to Group 10 metal is at least 0.1, or from at least 0.1 up to 10, preferably at least 0.5, more preferably at least 1. In one or more embodiments, the Group 11 metal is present as an oxide.

A preferred Group 9 metal is Rh, which may form an alloy with the Group 10 metal. Preferably, the molar ratio of Rh to Group 10 metal is in the range from 0.1 to 5.

In one or more embodiments of aluminosilicates, the molar ratio of said Group 1 alkali metal to Al is at least 0.5, or from at least 0.5 up to 3, preferably at least 1, more preferably at least 2.

In one or more embodiments of aluminosilicates, the molar ratio of said Group 2 alkaline earth metal to Al is at least 0.5, or from at least 0.5 up to 3, preferably at least 1, more preferably at least 2.

In one or more embodiments, the catalyst composition has an Alpha Value (as measured prior to the addition of the Group 10 metal, preferably platinum) of less than 25, alternately less than 15, alternately from 1 to 25, alternately from 1.1 to 15.

In one or more embodiments, the use of any one of the catalyst compositions of this invention provides a conversion of at least 70%, or at least 75%, or at least 80%, or in the range from 60% to 80%, of said acyclic $C_5$ feedstock under acyclic $C_5$ conversion conditions. This includes an n-pentane containing feedstock with equimolar $H_2$, a temperature in the range of 550° C. to 600° C., an n-pentane partial pressure between 3 and 10 psia, and an n-pentane weight hourly space velocity of 10 to 20 $hr^{-1}$.

In one or more embodiments, the use of any one of the catalyst compositions of this invention provides a carbon selectivity to cyclic $C_5$ compounds of at least 30%, or at least 40%, or at least 50%, or in the range from 30% to 80%, under acyclic $C_5$ conversion conditions. This includes an n-pentane feedstock with equimolar $H_2$, a temperature in the range of 550° C. to 600° C., an n-pentane partial pressure between 3 and 10 psia, and an n-pentane weight hourly space velocity between 10 and 20 $hr^{-1}$.

In one or more embodiments, the use of any one of the catalyst compositions of this invention provides a carbon selectivity to cyclopentadiene of at least 30%, or at least 40%, or at least 50%, or in the range from 30% to 80%, under acyclic $C_5$ conversion conditions. This includes an n-pentane feedstock with equimolar $H_2$, a temperature in the range of 550° C. to 600° C., an n-pentane partial pressure between 3 and 10 psia, and an n-pentane weight hourly space velocity between 10 and 20 $hr^{-1}$.

The catalyst compositions of this invention can be combined with a matrix or binder material to render them attrition resistant and more resistant to the severity of the conditions to which they will be exposed during use in hydrocarbon conversion applications. Preferred binder materials comprise one or more of silica, titania, zirconia, metal silicates of Group 1 or Group 13 of the Periodic Table, carbides, nitrides, aluminum phosphate, aluminum molybdate, aluminate, surface passivated alumina, and mixtures thereof. Preferably, suitable binder materials have a lower affinity for Group 10 metal particles, e.g. Pt, in comparison with the crystalline metallosilicate, e.g. aluminosilicate. The combined compositions can contain 1 to 99 wt % of the materials of the invention based on the combined weight of the matrix (binder) and material of the invention. The relative proportions of microcrystalline material and matrix may vary widely, with the crystal content ranging from 1 to 90 wt % and, more usually, particularly when the composite is prepared in the form of beads, extrudates, pills, oil drop formed particles, spray dried particles, etc., in the range of 2 to 80 wt % of the composite.

Useful catalyst compositions comprise a crystalline aluminosilicate or ferrosilicate, which is optionally combined with one, two, or more additional metals or metal compounds. Preferred combinations include:
1) a crystalline aluminosilicate (such as ZSM-5 or Zeolite L) combined with a Group 10 metal (such as Pt), a Group 1 alkali metal (such as sodium or potassium) and/or a Group 2 alkaline earth metal;
2) a crystalline aluminosilicate (such as ZSM-5 or Zeolite L) combined with a Group 10 metal (such as Pt), and a Group 1 alkali metal (such as sodium or potassium);
3) a crystalline aluminosilicate (such as a ferrosilicate or an iron treated ZSM-5) combined with a Group 10 metal (such as Pt) and a Group 1 alkali metal (such as sodium or potassium);
4) a crystalline aluminosilicate (Zeolite L) combined with a Group 10 metal (such as Pt) and a Group 1 alkali metal (such as potassium); and
5) a crystalline aluminosilicate (such as ZSM-5) combined with a Group 10 metal (such as Pt), a Group 1 alkali metal (such as sodium), and a Group 11 metal (such as silver or copper).

Another useful catalyst composition is a Group 10 metal (such as Ni, Pd, and Pt, preferably Pt) supported on silica (e.g., silicon dioxide) modified by a Group 1 alkali metal silicate (such as Li, Na, K, Rb, and/or $C_S$ silicates) and/or a Group 2 alkaline earth metal silicate (such as Mg, Ca, Sr, and/or Ba silicates), preferably potassium silicate, sodium silicate, calcium silicate, and/or magnesium silicate, preferably potassium silicate and/or sodium silicate. The Group 10 metal content of the catalyst composition is at least 0.005 wt %, based on the weight of the catalyst composition, preferably, in the range from 0.005 wt % to 10 wt %, or from 0.005 wt % up to 1.5 wt %, based on the weight of the catalyst composition. The silica ($SiO_2$) may be any silica typically used as catalyst support such as those marketed under the tradenames of DAVISIL 646 (Sigma Aldrich), DAVISON 952, DAVISON 948 or DAVISON 955 (Davison Chemical Division of W.R. Grace and Company).

Catalyst composition shape and design are preferably configured to minimize pressure drop, increase heat transfer, and minimize mass transport phenomena. Suitable catalyst shape and design are described in WO 2014/053553, which is incorporated by reference in its entirety. The catalyst composition may be an extrudate with a diameter of 2 mm to 20 mm Optionally, the catalyst composition cross section may be shaped with one or more lobes and/or concave sections. Additionally, the catalyst composition lobes and/or concave sections may be spiraled. The catalyst composition may be an extrudate with a diameter of 2 mm to 20 mm; and the catalyst composition cross section may be shaped with one or more lobes and/or concave sections; and the catalyst composition lobes and/or concave sections may be spiraled. Also, the formulated catalyst composition may be made into a particle, such as, for example, a spray dried particle, an oil drop particle, a mulled particle, or a spherical particle. The formulated catalyst composition may be made into a slurry. Such slurry materials typically contain the microporous crystalline metallosilicate, such as zeolite, and a filler such as a silicate. For fluid bed reactors spherical particle shapes are particularly useful. For fluid bed reactors spherical particle shapes are particularly useful.

For more information on useful catalyst compositions, please see U.S. Publication Nos. 2017/0121253; 2017/0121245; 2017/0121254; 2017/0121247; and 2017/0121246, which are incorporated herein by reference.

Preferably, the catalyst material comprises platinum on ZSM-5, platinum on zeolite L, and/or platinum on silica.

Suitable amounts of catalyst material in the particulate material may be ≤1.0 wt %, ≤5.0 wt %, ≤10.0 wt %, ≤15.0 wt %, ≤20.0 wt %, ≤25.0 wt %, ≤30.0 wt %, ≤35.0 wt %, ≤40.0 wt %, ≤45.0 wt %, ≤50.0 wt %, ≤55.0 wt %, ≤60.0 wt %, ≤65.0 wt %, ≤70.0 wt %, ≤75.0 wt %, ≤80.0 wt %, ≤85.0 wt %, ≤90.0 wt %, ≤95.0 wt %, ≤99.0 wt % or 100.0 wt %. Additionally or alternatively, the particulate material may comprise the catalyst material in an amount of ≥1.0 wt %, ≥5.0 wt %, ≥10.0 wt %, ≥15.0 wt %, ≥20.0 wt %, ≥25.0 wt %, ≥30.0 wt %, ≥35.0 wt %, ≥40.0 wt %, ≥45.0 wt %, ≥50.0 wt %, ≥55.0 wt %, ≥60.0 wt %, ≥65.0 wt %, ≥70.0 wt %, ≥75.0 wt %, ≥80.0 wt %, ≥85.0 wt %, ≥90.0 wt %, or ≥95.0 wt %. Ranges expressly disclosed include combinations of any of the above-enumerated values; e.g., 1.0 wt % to 100.0 wt %, 5.0 wt % to 100.0 wt %, 10.0 wt % to 90.0 wt %, 20.0 wt % to 80.0 wt %, etc. Preferably, the particulate material may comprise the catalyst material in an amount of 5.0 wt % to 100 wt %, 5.0 wt % to 90.0 wt %, more preferably 10.0 wt % to 80.0 wt %, more preferably 20.0 wt % to 70.0 wt %, more preferably 25.0 wt % to 60.0 wt %, more preferably 30.0 wt % to 50.0 wt %.

In addition to the catalyst material, the particulate material may further comprise inert material, which may also be present within and/or at least partially coated on an interior channel of an electrically-conductive reaction zone. As referred to herein, the inert material is understood to include materials which promote a negligible amount (e.g., ≤3%, ≤2%, ≤1%, etc.) of conversion of the feedstock, intermediate products, or final products under the reaction conditions described herein. The catalyst material and the inert material may be combined as portions of the same particles and/or may be separate particles. Preferably the catalyst material and the inert material are separate particles. Additionally, the catalyst material and/or inert material may be essentially spherical (i.e., <20%, <30%, <40%, or <50% aberration in diameter). Examples of suitable inert materials include, but are not limited to metal carbides (e.g., silicon carbide, tungsten carbide, etc.), metal oxides (e.g., silica, zirconia, titania, alumina, etc.), clays, metal phosphates (e.g., aluminum phosphates, nickel phosphates, zirconium phosphates, etc.), and combinations thereof. In particular, the inert material may comprise silicon carbide, silica, and a combination thereof.

Suitable amounts of inert material in the particulate material may be 0.0 wt %, ≥1.0 wt %, ≥5.0 wt %, ≥10.0 wt %, ≥15.0 wt %, ≥20.0 wt %, ≥25.0 wt %, ≥30.0 wt %, ≥35.0 wt %, ≥40.0 wt %, ≥45.0 wt %, ≥50.0 wt %, ≥55.0 wt %, ≥60.0 wt %, ≥65.0 wt %, ≥70.0 wt %, ≥75.0 wt %, ≥80.0 wt %, ≥85.0 wt %, ≥90.0 wt %, ≥95.0 wt %, or ≥99.0 wt %. Additionally or alternatively, the particulate material may comprise an inert material in an amount of ≤1.0 wt %, ≤5.0 wt %, ≤10.0 wt %, ≤15.0 wt %, ≤20.0 wt %, ≤25.0 wt %, ≤30.0 wt %, ≤35.0 wt %, ≤40.0 wt %, ≤45.0 wt %, ≤50.0 wt %, ≤55.0 wt %, ≤60.0 wt %, ≤65.0 wt %, ≤70.0 wt %, ≤75.0 wt %, ≤80.0 wt %, ≤85.0 wt %, ≤90.0 wt %, ≤95.0 wt %, or ≤99.0 wt %. Ranges expressly disclosed include combinations of any of the above-enumerated values, e.g., 0.0 wt % to 99.0 wt %, 0.0 wt % to 95.0 wt %, 10.0 wt % to 90.0 wt %, 20.0 wt % to 80.0 wt %, etc. Preferably, the particulate material may comprise an inert material in an amount of 0.0 wt % to 95.0 wt %, more preferably 0.0 wt % to 90.0 wt %, more preferably 30.0 wt % to 85.0 wt %.

iv. Effluent

An effluent (e.g., first effluent, second effluent) exiting an electrically-conductive reaction zone may comprise a variety of hydrocarbon compositions produced from the reaction of the acyclic hydrocarbons (e.g., acyclic $C_5$ hydrocarbons) in the one or more reaction zones. The hydrocarbon compositions typically have mixtures of hydrocarbon compounds, such as alkenes, cyclic hydrocarbons, and aromatics, having from 1 to 30 carbon atoms ($C_1$-$C_{30}$ hydrocarbons), from 1 to 24 carbon atoms ($C_1$-$C_{24}$ hydrocarbons), from 1 to 18 carbon atoms ($C_1$-$C_{18}$ hydrocarbons), from 1 to 10 carbon atoms ($C_1$-$C_{10}$ hydrocarbons), from 1 to 8 carbon atoms ($C_1$-$C_8$ hydrocarbons), and from 1 to 6 carbon atoms ($C_1$-$C_6$ hydrocarbons). Particularly, the first effluent comprises cyclopentadiene. The cyclopentadiene may be present in a hydrocarbon portion of an effluent (e.g., first effluent, second effluent) in an amount of ≥20.0 wt %, ≥25.0 wt %, ≥30.0 wt %, ≥35.0 wt %, ≥40.0 wt %, ≥45.0 wt %, ≥50.0 wt %, ≥55.0 wt %, ≥60.0 wt %, ≥65.0 wt %, ≥70.0 wt %, ≥75.0 wt %, or ≥80.0 wt %. Additionally or alternatively, the cyclopentadiene may be present in a hydrocarbon portion of an effluent (e.g., first effluent, second effluent) in an amount of ≤20.0 wt %, ≤25.0 wt %, ≤30.0 wt %, ≤35.0 wt %, ≤40.0 wt %, ≤45.0 wt %, ≤50.0 wt %, ≤55.0 wt %, ≤60.0 wt %, ≤65.0 wt %, ≤70.0 wt %, ≤75.0 wt %, ≤80.0 wt %, or ≤85.0 wt %. Ranges expressly disclosed include combinations of any of the above-enumerated values, e.g., 20.0 wt % to 85.0 wt %, 30.0 wt % to 75.0 wt %, 40.0 wt % to 85.0 wt %, 50.0 wt % to 85.0 wt %, etc. Preferably, the cyclopentadiene may be present in a hydrocarbon portion of an effluent (e.g., first effluent, second effluent) in an amount of 10.0 wt % to 85.0 wt %, more preferably 25.0 wt % to 80.0 wt %, more preferably 40.0 wt % to 75.0 wt %.

In other aspects, an effluent (e.g., first effluent, second effluent) may comprise one or more other $C_5$ hydrocarbons in addition to cyclopentadiene. Examples of other $C_5$ hydrocarbons include, but are not limited to cyclopentane and cyclopentene. The one or more other $C_5$ hydrocarbons may be present in a hydrocarbon portion of an effluent (e.g., first effluent, second effluent) in an amount ≥10.0 wt %, ≥15.0 wt %, ≥20.0 wt %, ≥25.0 wt %, ≥30.0 wt %, ≥35.0 wt %, ≥40.0 wt %, ≥45.0 wt %, ≥50.0 wt %, ≥55.0 wt %, ≥60.0 wt %, ≥65.0 wt %, or ≥70.0 wt %. Additionally or alternatively, the one or more other $C_5$ hydrocarbons may be present in a hydrocarbon portion of an effluent (e.g., first effluent, second effluent) in an amount of ≤15.0 wt %, ≤20.0 wt %, ≤25.0 wt %, ≤30.0 wt %, ≤35.0 wt %, ≤40.0 wt %, ≤45.0 wt %, ≤50.0 wt %, ≤55.0 wt %, ≤60.0 wt %, ≤65.0 wt %, or ≤70.0 wt %. Ranges expressly disclosed include combinations of any of the above-enumerated values, e.g., 10.0 wt % to 70.0 wt %, 10.0 wt % to 55.0 wt %, 15.0 wt % to 60.0 wt %, 25.0 wt % to 65.0 wt %, etc. Preferably, the one or more other $C_5$ hydrocarbons may be present in a hydrocarbon portion of an effluent (e.g., first effluent, second effluent) in an amount of 30.0 wt % to 65.0 wt %, more preferably 20.0 wt % to 40.0 wt %, more preferably 10.0 wt % to 25.0 wt %.

In other aspects, an effluent (e.g., first effluent, second effluent) may also comprise one or more aromatics, e.g., having 6 to 30 carbon atoms, particularly 6 to 18 carbon atoms. The one or more aromatics may be present in a hydrocarbon portion of an effluent (e.g., first effluent, second effluent) in an amount of ≥1.0 wt %, ≥5.0 wt %, ≥10.0 wt %, ≥15.0 wt %, ≥20.0 wt %, ≥25.0 wt %, ≥30.0 wt %, ≥35.0 wt %, ≥40.0 wt %, ≥45.0 wt %, ≥50.0 wt %, ≥55.0 wt %, ≥60.0 wt %, or ≥65.0 wt %. Additionally or alternatively, the one or more aromatics may be present in a hydrocarbon portion of an effluent (e.g., first effluent, second effluent) in an amount of ≤1.0 wt %, ≤5.0 wt %, ≤10.0 wt %, ≤15.0 wt %, ≤20.0 wt %, ≤25.0 wt %, ≤30.0 wt %, ≤35.0 wt %, ≤40.0 wt %, ≤45.0 wt %, ≤50.0 wt %, ≤55.0 wt %, ≤60.0 wt %, or ≤65.0 wt %. Ranges expressly disclosed include combinations of any of the above-enumerated values, e.g., 1.0 wt % to 65.0 wt %, 10.0 wt % to 50.0 wt %, 15.0 wt % to 60.0 wt %, 25.0 wt % to 40.0 wt %, etc. Preferably, the one or more aromatics may be present in a hydrocarbon portion of an effluent (e.g., first effluent, second effluent) in an amount of 1.0 wt % to 15.0 wt %, more preferably 1.0 wt % to 10 wt %, more preferably 1.0 wt % to 5.0 wt %. For information on possible dispositions of the effluents, please see U.S. Publication 2017/0121243; 2017/0121255; 2017/0121248; and 2017/0121244, which are incorporated herein by reference.

B. Rejuvenation Cycle

During the reaction step, coke material may form on the particulate material, particularly on the catalyst material, which may reduce the activity of the catalyst material. Additionally or alternatively, the particulate material may cool as the reaction occurs. This catalyst material at the end of a reaction step with coke formation and/or having a reduced temperature is referred to as a "spent catalyst material."

Thus, the process may further comprise a rejuvenation cycle where the feedstock at an electrically-conductive reaction zone may be cyclically halted and a rejuvenating gas may be provided to the reaction zone to the reactor system. In various aspects, the rejuvenating gas may provide heat to reheat the particulate material. Alternatively or additionally, the heat for heating the particulate material (e.g., spent catalyst material) may be provided by the electrical heating of the electrically-conductive reaction zone, e.g., monolith.

In various aspects, the particulate material (e.g., spent catalyst material) may be contacted with a hydrogen-containing rejuvenation gas comprising hydrogen and substantially free of reactive oxygen-containing compounds to remove at least a portion of incrementally deposited coke material on the catalyst material thereby forming a rejuvenated catalyst material within the electrically-conductive reaction zone and optionally, a volatile hydrocarbon, such as, but not limited to methane In such aspects, heat for removing the incrementally deposited coke material may be preferably provided by the electrical heating of the electrically-conductive reaction zone, e.g., monolith.

As used herein, the term "incrementally deposited" coke material refers to an amount of coke material that is deposited on the catalyst material during each pass of the catalyst material through the one or more reaction zones as opposed to a cumulative amount of coke material deposited on the catalyst material during multiple passes through the one or more reaction zones. "Substantially free" used in this context means the rejuvenation gas comprises less than 1.0 wt %, based upon the weight of the gaseous stream, e.g., less than 0.1 wt %, less than 0.01 wt %, less than 0.001 wt %, less than 0.0001 wt %, less than 0.00001 wt % oxygen-containing compounds.

The hydrogen-containing rejuvenation gas may comprise ≥50 wt % $H_2$, such as ≥60 wt %, ≥70 wt %, preferably ≥90 wt % $H_2$. The rejuvenation gas may further comprise an inert substance (e.g., $N_2$), and/or methane. After a suitable duration, the hydrogen-containing rejuvenation gas and, optionally, the volatile hydrocarbon, may exit an electrically-conductive reaction zone via an outlet. The hydrogen-containing rejuvenation gas may comprise ≥50 wt % $H_2$, such as ≥60 wt %, ≥70 wt %, preferably ≥90 wt % $H_2$. The hydrogen-containing rejuvenation gas may enter an electrically-conductive reaction zone and/or the rejuvenation cycle may be operated at a temperature of ≥400° C., ≥450° C., ≥500° C., ≥550° C., ≥600° C., ≥650° C., ≥700° C., ≥750° C., ≥800° C., ≥850° C., or ≥900° C. Preferably, the hydrogen-containing rejuvenation gas may enter an electrically-conductive reaction zone and/or the rejuvenation cycle may be operated at a temperature of ≥600° C. Additionally or alternatively, the hydrogen-containing rejuvenation gas may enter an electrically-conductive reaction zone and/or the rejuvenation cycle may be operated at a temperature of ≤400° C., ≤450° C., ≤500° C., ≤550° C., ≤600° C., ≤650° C., ≤700° C., ≤750° C., ≤800° C., ≤850° C., or ≤900° C. Ranges of temperatures expressly disclosed include combinations of any of the above-enumerated values, e.g., 400° C. to 900° C., 450° C. to 850° C., 500° C. to 800° C., etc. Preferably, the rejuvenation gas may enter an electrically-conductive reaction zone and/or the rejuvenation cycle may be operated at a temperature of 400° C. to 800° C., more preferably 600° C. to 800° C., more preferably 625° C. to 700° C., more preferably 550° C. to 750° C.

Additionally or alternatively, the hydrogen-containing rejuvenation gas may enter an electrically-conductive reaction zone and/or the rejuvenation cycle may be operated at a pressure of ≥1.0 psia, ≥5.0 psia, ≥25.0 psia, ≥50.0 psia, ≥75.0 psia, ≥100.0 psia, ≥125.0 psia, ≥150.0 psia, ≥175.0 psia, ≥200.0 psia, ≥225.0 psia, ≥250.0 psia, ≥275.0 psia, ≥300.0 psia, ≥325.0 psia, or ≥350.0 psia. Preferably, the hydrogen-containing rejuvenation gas may enter an electrically-conductive reaction zone and/or the rejuvenation cycle may be operated at a pressure of ≥100.0 psia. Additionally or alternatively, the hydrogen-containing rejuvenation gas may enter an electrically-conductive reaction zone and/or the rejuvenation cycle may be operated at a pressure of ≤1.0 psia, ≤5.0 psia, ≤25.0 psia, ≤50.0 psia, ≤75.0 psia, ≤100.0 psia, ≤125.0 psia, ≤150.0 psia, ≤175.0, psia ≤200.0 psia, ≤225.0 psia, ≤250.0 psia, ≤275.0 psia, ≤300.0 psia, ≤325.0 psia, or ≤350.0 psia. Ranges of pressures expressly disclosed include combinations of any of the above-enumerated values, e.g., 1.0 psia to 350.0 psia, 5.0 psia to 275.0 psia, 25.0 psia to 250.0 psia, etc. In particular, the hydrogen-containing rejuvenation gas may enter an electrically-conductive reaction zone and/or the rejuvenation cycle may be operated at a pressure of 1 psia to 300 psia, more preferably 5 psia to 250 psia, more preferably 25 psia to 250 psia.

In alternative aspects, the particulate material (e.g., spent catalyst material) may be rejuvenated via a mild oxidation procedure comprising contacting the particulate material with an oxygen-containing rejuvenation gas under conditions effective to remove at least a portion of incrementally deposited coke material on the catalyst material thereby forming a rejuvenated catalyst material. Typically, these conditions include a temperature range of 250° C. to 500° C., and a total pressure of 0.1 bar to 100 bar, preferably at atmospheric pressure. Further, the oxygen-containing rejuvenation gas is typically supplied at a total WHSV in the range of 1 to 10,000. Following the mild oxidation, purge gas is generally reintroduced to purge oxidants from the catalyst composition using a purge gas, for example, $N_2$. This purging step may be omitted if $CO_2$ is the oxidant as it will not produce a flammable mixture. Optionally, rejuvenation via mild oxidation further comprises one or more hydrogen treatment steps.

In various aspects, the hydrogen or oxygen-containing rejuvenation gas may flow in a direction co-current or counter-current to a direction of a flow of the feedstock. For example, if the feedstock enters at a top portion of an electrically-conductive reaction zone during a reaction step, during the rejuvenation cycle, the rejuvenation gas may also enter at a top portion of an electrically-conductive reaction zone and thereby flow in a direction co-current to a direction of flow of the feedstock. Additionally or alternatively, if the feedstock enters at a top portion of an electrically-conductive reaction zone, during the rejuvenation interval, the rejuvenation gas may enter at a bottom portion of an electrically-conductive reaction zone and thereby flow in a direction counter-current to a direction of flow of the feedstock. Preferably, the rejuvenation gas flows in a direction counter-current to a direction of flow of the feedstock and/or an inverse temperature profile in the electrically-conductive reaction zone may be achieved.

Preferably, during the rejuvenation cycle, the incrementally deposited coke material is removed from the catalyst material in an amount of ≥1.0 wt %, ≥5.0 wt %, ≥10.0 wt %, ≥15.0 wt %, ≥20.0 wt %, ≥25.0 wt %, ≥30.0 wt %, ≥35.0 wt %, ≥40.0 wt %, ≥45.0 wt %, ≥50.0 wt %, ≥55.0 wt %, ≥60.0 wt %, ≥65.0 wt %, ≥70.0 wt %, ≥75.0 wt %, ≥80.0 wt %, ≥85.0 wt %, ≥90.0 wt %, ≥95.0 wt %, ≥99.0 wt %, or 100.0 wt %. Preferably, at least 10.0 wt % of the incrementally deposited coke material is removed from the catalyst material, more preferably at least 90.0 wt %, more preferably at least 95.0 wt %, more preferably at least 99.0 wt %. Additionally or alternatively, the incrementally deposited coke material is removed from the catalyst material in an amount of ≤1.0 wt %, ≤5.0 wt %, ≤10.0 wt %, ≤15.0 wt %, ≤20.0 wt %, ≤25.0 wt %, ≤30.0 wt %, ≤35.0 wt %, ≤40.0 wt %, ≤45.0 wt %, ≤50.0 wt %, ≤55.0 wt %, ≤60.0 wt %, ≤65.0 wt %, ≤70.0 wt %, ≤75.0 wt %, ≤80.0 wt %, ≤85.0 wt %, ≤90.0 wt %, ≤95.0 wt %, ≤99.0 wt %, or 100.0 wt %. Ranges expressly disclosed include combinations of any of the above-enumerated values, e.g., 1.0 wt % to 100.0 wt %, 5.0 wt % to 95.0 wt %, 10.0 wt % to 90.0 wt %, 30.0 wt % to 90.0 wt %, etc. Preferably, the incrementally deposited coke material is removed from the catalyst material in an amount of 1.0 wt % to 100.0 wt %, more preferably 10.0 wt % to 100.0 wt %, more preferably 90.0 wt % to 100.0 wt %, more preferably 95.0 wt % to 100.0 wt %.

Preferably, the rejuvenation cycle may have a duration of ≥1 min, ≥5 min, ≥10 min, ≥15 min, ≥20 min, ≥25 min, ≥30 min, ≥35 min, ≥40 min, ≥45 min, ≥50 min, ≥55 min, ≥60 min, ≥65 min, ≥70 min, ≥75 min, ≥80 min, ≥85 min, ≥90 min, ≥95 min, ≥100 min, ≥110 min or ≥120 min Additionally or alternatively, the reheating interval may have a duration of ≤1 min, ≤5 min, ≤10 min, ≤15 min, ≤20 min, ≤25 min, ≤30 min, ≤35 min, ≤40 min, ≤45 min, ≤50 min, ≤55 min, ≤60 min, ≤65 min, ≤70 min, ≤75 min, ≤80 min, ≤85 min, ≤90 min, ≤95 min, ≤100 min, ≤110 min or ≤120 min Ranges expressly disclosed include combinations of any of the above-enumerated values, e.g., 1 to 120 min, 1 to 90 min, 4 to 80 min, 10 to 75 min, etc. Preferably, the rejuvenation cycle may have a duration of 1 to 120 min, more preferably 1 to 90 min, more preferably 1 to 60 min, more preferably 5 to 40 min. Preferably, the duration of the rejuvenation cycle may be less than the duration of the reaction step; more preferably, the duration of the rejuvenation cycle may be less than one half the duration of the reaction step.

In various aspects, the hydrogen or oxygen-containing rejuvenation gas may be heated using the electrical heating of the electrically-conductive reaction zone, e.g., monolith. Additionally or alternatively, rejuvenation gas is provided by a suitable apparatus, such as, but not limited to a fire heater. In the apparatus, the rejuvenation gas may be heated to a suitable temperature as described above prior to providing the rejuvenation gas to an electrically-conductive reaction zone. Additionally or alternatively, the rejuvenation gas exiting an electrically-conductive reaction zone may also be returned to the apparatus to be reheated to a suitable temperature as described above and then provided to an electrically-conductive reaction zone. Additionally or alternatively, volatile hydrocarbons (gasification products formed during rejuvenation) are separated from the rejuvenation effluent gas after exiting an electrically-conductive reaction zone. In such aspects the resulting hydrogen-rich product separated from the rejuvenation effluent gas is generally returned to the apparatus to be reheated to a suitable temperature as described above and then provided to an electrically-conductive reaction zone. The apparatus may also make steam and/or heat the feedstock prior to the feedstock entering an electrically-conductive reaction zone.

C. Regeneration Cycle

The process may further comprise a regeneration cycle to recapture catalyst activity lost due to the accumulation of coke material and/or agglomeration of metal on the catalyst material during the reaction. This regeneration cycle may be carried out when there has not been sufficient removal of the coke material from the particulate material (e.g., spent catalyst material) during the rejuvenation cycle(s). For example, catalyst activity in an electrically-conductive reaction zone may be restored to above 50% of the fresh catalyst activity, preferably above 80% of the fresh catalyst activity, and most preferably above 95% and below 99.9% of the fresh catalyst activity.

During the regeneration cycle, the feedstock may be cyclically halted to an electrically-conductive reaction zone. After halting the feedstock, purging of any combustible gas optionally may be performed. For example, feedstock and/or reactor product (e.g., cyclopentadiene) may be purged. For example, if a combustible gas was present in the electrically-conductive reaction zone and it is desired to introduce an oxidant, the system is generally first purged with an inert to reduce combustible gas concentration.

The particulate material, particularly catalyst material, may then be regenerated by methods known in the art. For example, an oxidative regeneration may be used to remove at least a portion of coke material from the spent catalyst material. In various aspects, a regeneration gas comprising an oxidizing material such as oxygen, for example, air, may contact the spent catalyst material. The regeneration gas may oxidatively remove at least 10 wt % (≥10 wt %) of coke material present at the start of regeneration. Typically, an oxychlorination step is performed following coke removal comprising contacting the catalyst composition with a gaseous stream comprising a chlorine source and an oxygen source under conditions effective for dispersing at least a portion of metal, e.g., Group 10 metal particles on the surface of the catalyst and to produce a metal chlorohydrate, e.g., a Group 10 metal chlorohydrate. Additionally, a chlorine stripping step is typically performed following oxychlorination comprising contacting the catalyst composition with a gaseous stream comprising an oxygen source, and optionally a chlorine source, under conditions effective for increasing the O/Cl ratio of the metal chlorohydrate. Generally, a reduction step, and optionally a sulfidation step may also be performed in the regeneration step. The gaseous streams employed during regeneration may flow in a direction counter-current or co-current to a direction of flow of the feedstock as described above for the rejuvenation gas. The regeneration gas may further comprise an inert substance (e.g., $N_2$) as well. Following regeneration, the catalyst material may be contacted with a purge gas, e.g., $N_2$. Once purging is complete, feedstock may then be provided to the electrically-conductive reaction zone.

Preferably, the regeneration cycle may have a duration of ≥0.5 day, ≥1 day, ≥1.5 days, ≥2 days, ≥3 days, ≥4 days, ≥5 days, ≥6 days, ≥7 days, ≥8 days, ≥9 days, ≥10 days, ≥11 days, ≥12 days, ≥13 days, ≥14 days, or ≥15 days. As used herein, the term "day" refers to an 24 hour period, and the term "0.5 day" refers to an 12 hour period. Additionally or alternatively, the regeneration cycle may have a duration of ≤0.5 day, ≤1 day, ≤1.5 days, ≤2 days, ≤3 days, ≤4 days, ≤5 days, ≤6 days, ≤7 days, ≤8 days, ≤9 days, ≤10 days, ≤11 days, ≤12 days, ≤13 days, ≤14 days, or ≤15 days. Ranges expressly disclosed include combinations of any of the above-enumerated values, e.g., 0.5 to 15 days, 1 to 12 days, 2 to 11 days, etc. Preferably, the regeneration cycle may have a duration of 1 to 15 days, more preferably 1 to 10 days, more preferably 1.5 to 5 days.

In various aspects, the regeneration cycle may be performed at a frequency of every 1 day, every 2 days, every 4 days, every 6 days, every 8 days, every 10 days, every 12 days, every 14 days, every 16 days, every 18 days, every 20 days, every 22 days, every 24 days, every 26 days, every 28 days, every 30 days, every 35 days, every 40 days, every 45 days, or every 50 days. Ranges expressly disclosed include combinations of any of the above-enumerated values, e.g., 1 to 50 days, 1 to 45 days, 2 to 35 days, etc. Preferably, the regeneration cycle may be performed at a frequency of every 1 to 50 days, more preferably every 10 to 45 days, more preferably every 20 to 40 days, more preferably every 30 to 35 days. Preferably, the regeneration cycle may be performed at a frequency of 1 to 50 days, more preferably 10 to 45 days, more preferably 20 to 40 days, more preferably 30 to 35 days.

As discussed above, the reactor system may comprise multiple electrically-conductive reaction zones, which may be operated in parallel. These electrically-conductive reaction zones may alternate operating in a reaction step, a rejuvenation cycle, and/or a regeneration cycle. In particular, the process described herein may comprise a second electrically-conductive reaction zone and a third electrically-conductive reaction zone operated in parallel with a first electrically-conductive reaction zone. During a reaction step in the first electrically-conductive reaction zone, a reaction step, a rejuvenation cycle and/or a regeneration cycle may be performed in the second electrically-conductive reaction zone and/or the third electrically-conductive reaction zone. For example, during a reaction step in the first electrically-conductive reaction zone, a rejuvenation cycle may be performed in the second electrically-conductive reaction zone. Additionally, a regeneration interval may be performed in the third electrically-conductive reaction zone Optionally, a reaction step in the second electrically-conductive reaction zone and a reaction step in the third electrically-conductive reaction zone may be performed, wherein the reaction step in the first electrically-conductive reaction zone, the reaction step in the second electrically-conductive reaction zone, and the reaction step in the third electrically-conductive reaction zone may be performed in a staggered fashion (i.e., be performed at different times).

III. Reaction Systems for Conversion of Acyclic Hydrocarbons

In another embodiment, a reaction system 1 for converting acyclic hydrocarbons (e.g., acyclic $C_5$ hydrocarbons) to alkenes, cyclic hydrocarbons (e.g., cyclopentadiene) and/or aromatics is provided, as shown FIG. 1. The reaction system 1 may comprise a feedstock stream 2 comprising acyclic hydrocarbons (e.g., acyclic $C_5$ hydrocarbons, such as pentane) as described above, an electrically-conductive reaction zone 3 as described above comprising a catalyst material as described above present within and/or at least partially coated on an interior channel of the electrically-conductive reaction zone 3, and an effluent stream 4 comprising alkenes, cyclic hydrocarbons (e.g., cyclopentadiene), and/or aromatics. Optionally, the reaction system 1 may further comprise additional electrically-conductive reaction zones, such as electrically-conductive reaction zone 8. In such aspects, the electrically-conductive reaction zones are generally in fluid connection with one another. For example, in reaction system 1, electrically-conductive reaction zone 8 is in fluid connection with electrically-conductive reaction zone 3 via stream 9. In various aspects, the catalyst material may be present as a layer having a thickness of 10 μm to 500 μm on the interior channel of the electrically-conductive reaction zone 3. The reaction system 1 may comprise a feedstock stream inlet (not shown) for providing the feedstock stream 2 to the reaction system and an effluent stream outlet (not shown) for removal of the first effluent stream 4. Optionally, a first hydrogen or light hydrocarbon co-feed stream 5 may be co-fed with the feedstock stream 2. The reaction system 1 may further comprise a means 6 for applying an electrical current to the electrically-conductive reaction zone 3 and two or more electrodes in contact with the electrically-conductive reaction zone 3 (not shown). Optionally, the reaction system 1 may further comprise additional means for applying an electrical current, such as in aspects where the reaction system 1 comprises multiple electrically-conductive reaction zones. For example, reaction system 1 may further comprise a means 7 for applying an electrical current to electrically-conductive reaction zone 8 and two or more electrodes in contact with the electrically-conductive reaction zone 8 (not shown).

The one or more electrically-conductive reaction zones of reaction system 1, such as electrically-conductive reaction zones 3 and 8, may independently be a monolith reactor formed from a ceramic or metallic material as described herein, for example, the ceramic material may be selected from the group consisting of silicon carbide, aluminum nitride, boron nitride, tungsten carbide, a MAX phase alloy, an ferrochrome alloy and a combination thereof. Additionally or alternatively, preferably, the reaction system 1 includes 1 to 50 electrically-conductive reactors, more preferably 1 to 40 electrically-conductive reactors, more preferably 10 to 40 electrically-conductive reactors.

The one or more electrically-conductive reaction zones of reaction system 1, such as electrically-conductive reaction zones 3 and 8, are operated under reaction conditions as described above to convert at least a portion of the acyclic hydrocarbons (e.g., acyclic $C_5$ hydrocarbons) to alkenes, cyclic hydrocarbons (e.g., cyclopentadiene), and/or aromatics. For example, the reaction conditions may comprise a temperature of 400° C. to 700° C. and/or a pressure of 3.0 psia to 100 psia. Additionally, the feedstock stream 2 may have a temperature of less than 650° C. and/or the effluent stream 4 may have a temperature of at least 550° C. Preferably, at least 30 wt % of the acyclic $C_5$ hydrocarbons is converted to cyclopentadiene. Optionally, the one or more electrically-conductive reaction zones of reaction system 1, such as electrically-conductive reaction zones 3 and 8, may include one or more heating devices (e.g., fired tube, heated coil) (not shown) in order to maintain temperature therein.

IV. Industrial Applicability

A hydrocarbon reactor effluent obtained during the acyclic $C_5$ conversion process containing cyclic, branched and linear $C_5$ hydrocarbons and, optionally, containing any combination of hydrogen, $C_4$ and lighter byproducts, or $C_6$ and heavier byproducts is a valuable product in and of itself. Preferably, CPD and/or DCPD may be separated from the reactor effluent to obtain purified product streams which are useful in the production of a variety of high value products.

For example, a purified product stream containing 50 wt % or greater, or preferably 60 wt % or greater of DCPD is useful for producing hydrocarbon resins, unsaturated polyester resins, and epoxy materials. A purified product stream containing 80 wt % or greater, or preferably 90 wt % or greater of CPD is useful for producing Diels-Alder reaction products formed in accordance with the following reaction Scheme (I):

Scheme I

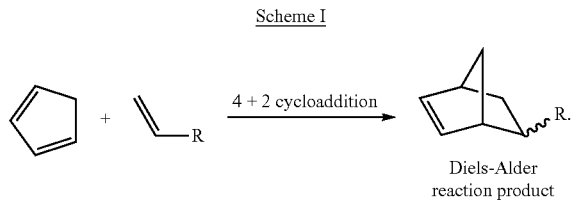

Diels-Alder reaction product where R is a heteroatom or substituted heteroatom, substituted or unsubstituted $C_1$-$C_{50}$ hydrocarbyl radical (often a hydrocarbyl radical containing double bonds), an aromatic radical, or any combination thereof. Preferably, substituted radicals or groups contain one or more elements from Groups 13-17, preferably from Groups 15 or 16, more preferably nitrogen, oxygen, or sulfur. In addition to the mono-olefin Diels-Alder reaction product depicted in Scheme (I), a purified product stream containing 80 wt % or greater, or preferably 90 wt % or greater of CPD can be used to form Diels-Alder reaction products of CPD with one or more of the following: another CPD molecule, conjugated dienes, acetylenes, allenes, disubstituted olefins, trisubstituted olefins, cyclic olefins, and substituted versions of the foregoing. Preferred Diels-Alder reaction products include norbornene, ethylidene norbornene, substituted norbornenes (including oxygen-containing norbornenes), norbornadienes, and tetracyclododecene, as illustrated in the following structures:

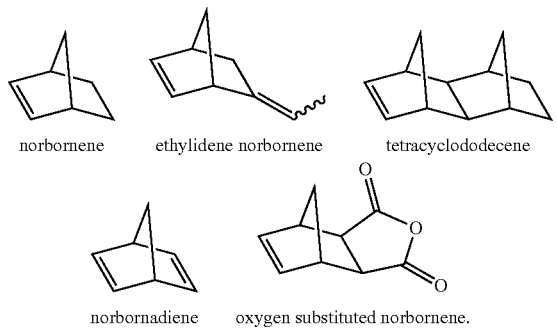

norbornene   ethylidene norbornene   tetracyclododecene norbornadiene   oxygen substituted norbornene.

The foregoing Diels-Alder reaction products are useful for producing polymers and copolymers of cyclic olefins copolymerized with olefins such as ethylene. The resulting cyclic olefin copolymer and cyclic olefin polymer products are useful in a variety of applications, e.g., packaging film.

A purified product stream containing 99 wt % or greater of DCPD is useful for producing DCPD polymers using, for example, ring opening metathesis polymerization (ROMP) catalysts. The DCPD polymer products are useful in forming articles, particularly molded parts, e.g., wind turbine blades and automobile parts.

Additional components may also be separated from the reactor effluent and used in the formation of high value products. For example, separated cyclopentene is useful for producing polycyclopentene, also known as polypentenamer, as depicted in Scheme (II).

Scheme II

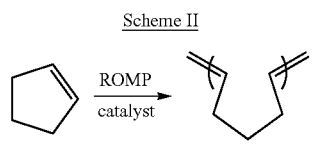

Separated cyclopentane is useful as a blowing agent and as a solvent. Linear and branched $C_5$ products are useful for conversion to higher olefins and alcohols. Cyclic and non-cyclic $C_5$ products, optionally after hydrogenation, are useful as octane enhancers and transportation fuel blend components.

PROPHETIC EXAMPLES

The following example is derived from modeling techniques and although the work was actually achieved, the inventors do not present these examples in the past tense to comply with M.P.E.P. § 608.01(p) if so required.

Reactor Performance Modeling

Reactor modeling was performed using Invensys Systems Inc. PRO/II 9.3.4 for the purpose of estimating the performance at various commercially relevant operating conditions. Depending on specifics of the modeling, variation in results will occur but the models will still demonstrate the relative benefits of the present invention. Numerous modifications and variations are possible and it is to be understood that within the scope of the claims, the invention may be practiced otherwise than as specifically described herein.

Example 1—Design of Electrically-Heated Monolith Reactor

The objective of the example is to determine approximate size and number of monoliths required to transfer the required heat duty as well as understand the required catalyst loading on a monolith to achieve a desired WHSV of 15 kg/kg/hr for producing 200 kTA of cyclopentadiene from pentane feed. A 20 psia outlet pressure, 575° C. outlet temperature reactor is simulated with a feed comprising n-pentane and co-feeds comprising methane and hydrogen, which are pre-heated to 621° C. prior to feeding into the monolith reactor. The hydrogen molar rate in the co-feed is set to deliver a molar ratio of hydrogen:n-pentane in feed of 1:1. The methane molar rate in the co-feed is set to deliver a methane partial pressure at reactor outlet of 10 psia (i.e., combined outlet partial pressure of all other hydrocarbons including hydrogen is 10 psia to give total outlet pressure of 20 psia). Based on the reactor yields, this corresponds to a molar ratio of methane:n-pentane in feed of 4:1. Under these conditions, the catalyst is assumed to have a lights selectivity ($C_{4-}$ products) of about 18%. The residence time within the monolith reactor (at WHSV of 15) is assumed to provide for CPD concentration to reach its thermodynamic concentration at reactor outlet conditions. To generate 1-lb mol of CPD in monolith reactor effluent under these conditions requires 2.195 lb-mol of n-pentane and heat input of 0.153 MMBtu or 161 MJ.

Figure 2:
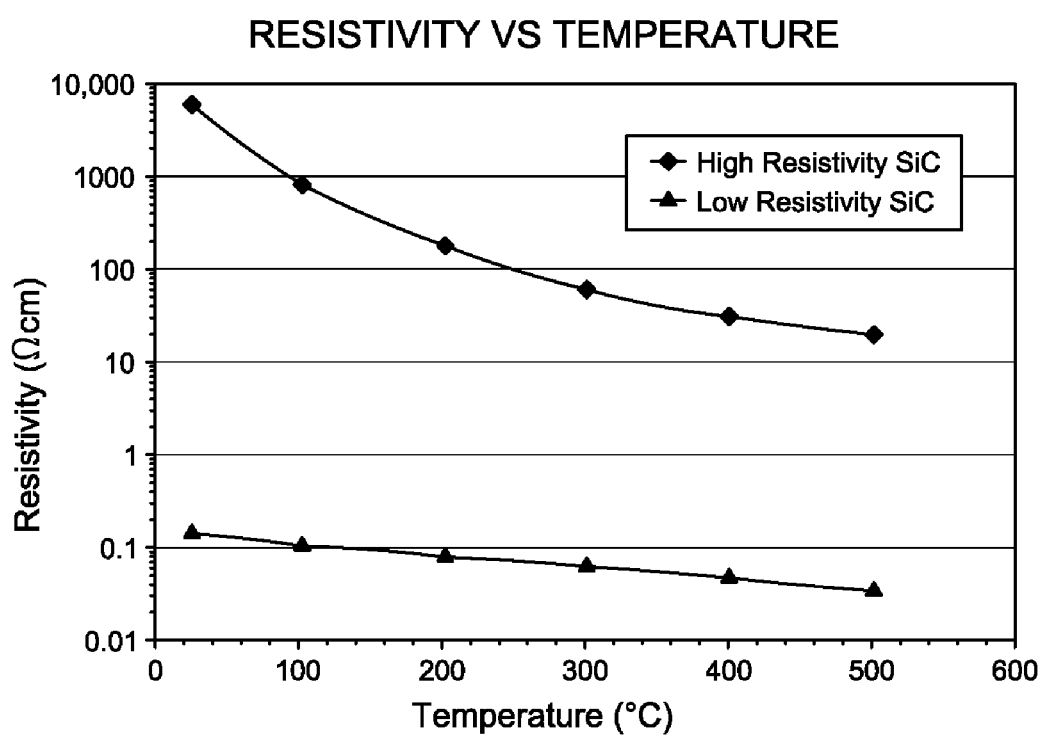
FIG. 2 illustrates low resistivity silicon carbide and high resistivity silicon carbide as temperature increases.

As shown below in Table 1, applying a 1000 V supply to 3'×3'×3' monolith cubes with resistivity of 15 ohm-cm (for high purity SiC at 500° C. in FIG. 2) resulted in about 35 monoliths arranged in series to supply the necessary heat as well as about 174 µm catalyst wash-coat thickness (for a WHSV of 15 kg/kg/hr).

TABLE 1

Design Calculations for Electrical Monolith Reactor

| | |
|---|---|
| Resistivity of SiC @ 500 C. | 15 omh-cm |
| Monolith Dimension | 3 ft × 3 ft × 3 ft |
| Monolith Axial Length (L) | 91 cm |
| Monolith Dimension (A; Parallel to Current) | 91 cm |
| Monolith Dimension (B) | 92 cm |
| Wall thickness or Honeycomb Monolith | 0.04 cm |
| # of cells per square inch | 100 cpsi |
| # of cells | 129600 |
| # of cells (in B dimension) | 360 |
| Total area for passage of current | 1320 cm2 |
| Resistance for one monolith | 104 ohm |
| Voltage applied | 1000 V |
| Current | 0.7 A/cm2 |
| Heat release rate in monolith | 962667 W |
| Gross monolith volume | 764555 cm3 |
| Geometric surface area on monolith | 6020117 cm2 |
| Heat release per unit monolith volume | 1.3 W/cm3 |
| Heat duty required | 116 MBtu/hr |
| Heat duty required | 33996378 W |
| Required monolith volume | 27000099 cm3 |
| Required monolith volume | 27 m3 |
| Required monolith dimension (for cube) | 3 m |
| # of Monoliths of 3' × 3' × 3' dimensions | 35 |
| Pentane feed rate | 54473 kg/hr |
| WHSV based on pentane | 15 kg/kg/hr |
| Catalyst Amount | 3632 kg |
| Catalyst Density | 984 kg/m3 |
| Catalyst Volume Required | 4 m3 |
| Total Surface Area Available for Washcoat | 21260 m2 |
| Thickness of Washcoat | 174 microns |

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

The invention claimed is:

1. A process for converting acyclic hydrocarbons to alkenes, cyclic hydrocarbons, and/or aromatics in a reactor system, wherein the process comprises:
   heating an electrically-conductive monolith reactor housed within the reactor system, said monolith reactor defining an electrically conductive reaction zone, by applying an electrical current to a plurality of electrodes in contact with the monolith reactor so that a direction of current flow through the monolith reactor is substantially orthogonal to a direction of flow of the feedstock through a channel within the monolith reactor; and
   contacting a feedstock comprising acyclic hydrocarbons with a catalyst material in the electrically-conductive reaction zone under reaction conditions sufficient to convert at least a portion of the acyclic hydrocarbons to an effluent comprising alkenes, cyclic hydrocarbons, and/or aromatics, wherein the catalyst material is at least partially coated on an interior of the channel of the zone monolith reactor.

2. The process of claim 1, wherein the catalyst material is present as a layer having a thickness of 10 μm to 500 μm on the interior of the channel.

3. The process of claim 1, wherein the heating includes substantially uniformly heating the monolith reactor with the electrical current, and method further comprises controlling an axial temperature profile of the monolith reactor by varying the electrical current applied to the monolith reactor.

4. The process of claim 1, wherein the feedstock is provided at a temperature of less than 650° C. and/or the effluent exiting the monolith reactor has a temperature of at least 550° C.

5. The process of claim 1, further comprising co-feeding hydrogen to the monolith reactor.

6. The process of claim 1, wherein the reaction conditions comprise a temperature of 400° C. to 700° C. and a pressure of 3 psia to 100 psia.

7. The process of claim 1, wherein the catalyst material comprises platinum on ZSM-5, platinum on zeolite L, and/or platinum on silica.

8. The process of claim 1, further comprising a rejuvenation cycle comprising:
   halting flow of the feedstock to the monolith reactor;
   rejuvenating the catalyst to produce to a rejuvenated catalyst material, optionally wherein the rejuvenation comprises contacting the catalyst material with a rejuvenation gas comprising hydrogen or oxygen; and
   resuming flow of the feedstock to the monolith reactor.

9. The process of claim 1, further comprising a regeneration cycle comprising:
   halting flow of the feedstock to the monolith reactor;
   regenerating the catalyst to produce a regenerated catalyst material; and
   resuming flow of the feedstock to the electrically-conductive reaction zone.

10. The process of claim 1, wherein the reactor system comprises two or more reactors operated in parallel or in series.

11. The process of claim 10, wherein the two or more monolith reactors are operated in series at independent temperatures.

12. The process of claim 10, wherein the two or more monolith reactors are formed of a ceramic material or a metallic material.

13. The process of claim 12, wherein the ceramic material is selected from the group consisting of silicon carbide, aluminum nitride, boron nitride, tungsten carbide, a MAX phase alloy, a ferrochrome alloy and a combination thereof.

14. The process of claim 10, wherein the reaction system comprises two or more monolith reactors operated in parallel.

15. The process of claim 1, wherein the acyclic hydrocarbons comprise acyclic $C_5$ hydrocarbons, and the cyclic hydrocarbons comprise cyclopentadiene.

16. The process of claim 15, wherein at least 30 wt. % of the acyclic $C_5$ hydrocarbons is converted to cyclopentadiene.

17. The process of claim 15, wherein the electrical current provides at least 25% of required heat for converting at least a portion of the acyclic $C_5$ hydrocarbons to the effluent comprising cyclopentadiene.

18. A reaction system adapted for converting acyclic hydrocarbons to alkenes, cyclic hydrocarbons, and/or aromatics, wherein the reaction system comprises:
   one or more electrically-conductive monolith reactors housed within the reactor system, the one or more monolith reactors being configured to convert, under reaction conditions, at least a portion of a feedstock stream including acyclic hydrocarbons to an effluent stream including alkenes, cyclic hydrocarbons, and/or aromatics, wherein the one or more monolith reactors each independently comprises:
   a catalyst material least partially coated on an interior channel of the monolith reactor;
   a feedstock stream inlet;
   an effluent stream outlet; and
   a current generator configured to supply a current to and heat the electrically-conductive reaction zone by supplying the current to a plurality of electrodes in contact with the monolith reactor so that a direction of current flow through the monolith reactor is substantially orthogonal to a direction of flow of the feedstock through the interior channel of the monolith reactor.

19. The reaction system of claim 18, wherein the one or more monolith reactors are formed from a ceramic material.

20. The reaction system of claim 19, wherein the ceramic material is selected from the group consisting of silicon carbide, aluminum nitride, boron nitride, tungsten carbide, a MAX phase alloy, an ferrochrome alloy and a combination thereof.

21. The reaction system of claim 18, wherein the catalyst material present as a layer on the interior channel has a thickness of 10 μm to 500 μm.

22. The reaction system of claim 18, wherein the reaction system comprises two or more monolith reactors configured in parallel.

23. The reaction system of claim 18, wherein the feedstock stream has a temperature of less than 650° C. and/or the effluent stream has a temperature of at least 550° C.

24. The reaction system of claim 18, wherein the acyclic hydrocarbons comprise acyclic $C_5$ hydrocarbons, and the cyclic hydrocarbons comprise cyclopentadiene.

* * * * *